(12) United States Patent  
Otake et al.

(10) Patent No.: US 10,207,976 B2  
(45) Date of Patent: Feb. 19, 2019

(54) METHOD FOR PRODUCING OPTICALLY ACTIVE 2-(2-FLUOROBIPHENYL-4-YL) PROPANOIC ACID

(71) Applicant: TAISHO PHARMACEUTICAL CO., LTD., Tokyo (JP)

(72) Inventors: Norikazu Otake, Tokyo (JP); Daisuke Matsuda, Tokyo (JP); Rie Shimono, Tokyo (JP); Hideaki Tabuse, Tokyo (JP); Minoru Moriya, Tokyo (JP); Yohei Kobashi, Tokyo (JP); Yohei Matsuda, Tokyo (JP); Tomokazu Tamaoki, Tokyo (JP)

(73) Assignee: TAISHO PHARMACEUTICAL CO., LTD, Tokyo (JP)

( * ) Notice: Subject to any disclaimer, the term of this patent is extended or adjusted under 35 U.S.C. 154(b) by 0 days.

(21) Appl. No.: 15/764,598

(22) PCT Filed: Sep. 29, 2016

(86) PCT No.: PCT/JP2016/078939  
§ 371 (c)(1),  
(2) Date: Mar. 29, 2018

(87) PCT Pub. No.: WO2017/057642  
PCT Pub. Date: Apr. 6, 2017

(65) Prior Publication Data  
US 2018/0282252 A1    Oct. 4, 2018

(30) Foreign Application Priority Data  
Sep. 30, 2015    (JP) .................................. 2015-194284

(51) Int. Cl.  
*C07C 51/09* (2006.01)  
*C07C 57/58* (2006.01)  
(Continued)

(52) U.S. Cl.  
CPC ............... *C07C 51/09* (2013.01); *B01J 27/10* (2013.01); *B01J 31/0244* (2013.01);  
(Continued)

(58) Field of Classification Search  
CPC ....... B01J 27/10; B01J 31/0244; C07C 51/09; C07C 67/343  
See application file for complete search history.

(56) References Cited

U.S. PATENT DOCUMENTS 3,959,364 A    5/1976 Armitage et al.

FOREIGN PATENT DOCUMENTS

CN    103755554    4/2014  
CN    103755566    4/2014  
(Continued)

OTHER PUBLICATIONS

JP2004-339085 translated (Year: 2004).*  
(Continued)

*Primary Examiner* — Yevgeny Valenrod  
*Assistant Examiner* — Blaine G Doletski  
(74) *Attorney, Agent, or Firm* — Finnegan, Henderson, Farabow, Garrett & Dunner, LLP

(57) ABSTRACT

A novel process for producing optically active 2-(2-fluoro-biphenyl-4-yl)propanoic acid is disclosed. This production process is characterized in that a compound of formula [1] is reacted with magnesium and so forth to prepare an organometallic reagent, which is reacted with a compound of formula [2] in the presence of a catalytic amount of a nickel compound and a catalytic amount of an optically active compound of formula [3] to obtain a compound represented by formula [4] which is subsequently converted to a compound represented by formula [5] or a pharmaceutically acceptable salt thereof.

[Formula 1]

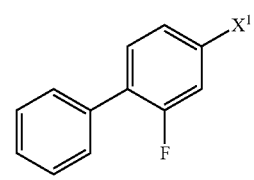

[1]

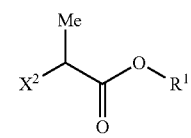

[2]

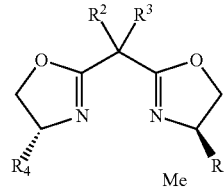

[3]

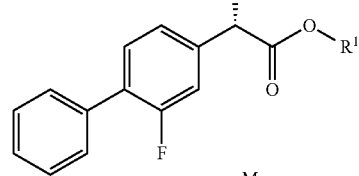

[4]

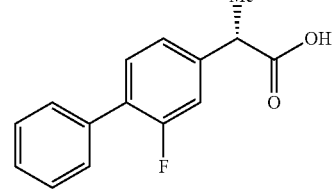

[5]

20 Claims, No Drawings

(51) Int. Cl.
*B01J 27/10* (2006.01)
*B01J 31/02* (2006.01)
*C07C 67/343* (2006.01)
*C07B 53/00* (2006.01)
*C07B 61/00* (2006.01)

(52) U.S. Cl.
CPC ............ *C07C 57/58* (2013.01); *C07C 67/343* (2013.01); *C07B 53/00* (2013.01); *C07B 61/00* (2013.01)

(56) References Cited

FOREIGN PATENT DOCUMENTS

| EP | 0110671 A | 6/1984 |
|---|---|---|
| EP | 2 712 858 A1 | 4/2014 |
| JP | 60-112735 | 6/1985 |
| JP | 2000-143580 A | 5/2000 |
| JP | 2004-339085 | 2/2004 |
| JP | 2004-339085 * | 12/2004 |
| JP | 2014-065693 | 4/2014 |

OTHER PUBLICATIONS

Mao et al. (Cobalt-Bisoxazoline-Catalyzed Asymmetric Kumada Cross-Coupling of Racemic α-Bromo Esters with Aryl Grignard Reagents, J. Amer. Chem. Soc., 136, pp. 17662-17668, Published Dec. 2014) (Year: 2014).*

S. Lou and G. Fu, "Nickel/Bis(oxazoline)-Catalyzed Asymmetric Kumada Reactions of Alkyl Electrophiles: Cross-Couplings of Racemic α-Bromoketones," *J. Am. Chem. Soc.* 132, pp. 1264-1266 (2010).

K. Dong, et al., "Asymmetric hydrogenation of α-arylacrylic and β-arylbut-3-enoic acids catalyzed by a Rh(I) complex of a monodentate secondary phosphine oxide ligand," *Org. Chem. Front.*, 1, pp. 155-160 (2014).

C. Fischer and G. Fu, "Asymmetric Nickel-Catalyzed Negishi Cross-Couplings of Secondary α-Bromo Amides with Organozinc Reagents," *J. Am. Chem. Soc.*, 127, pp. 4594-4595 (2005).

P. Lundin, et al., "Catalytic Asymmetric Cross-Couplings of Racemic α-Bromoketones with Arylzinc Reagents," *Angew. Chem. Int. Ed.*, 48, pp. 154-156 (2009).

J. Mao, et al., "Cobalt—Bisoxazoline-Catalyzed Asymmetric Kumada Cross-Coupling of Racemic α-Bromo Esters with Aryl Grignard Reagents," *J. Am. Chem. Soc.*, 136, pp. 17662-17668 (2014).

M. Jin, et al., "Iron-Catalyzed Enantioselective Cross-Coupling Reactions of α-Chloroesters with Aryl Grignard Reagents," *J. Am. Chem. Soc.*, 137, pp. 7128-7134 (2015).

Translation of Written Opinion of the International Searching Authority for PCT Application No. PCT/JP2016/078939, dated Apr. 3, 2018 (six pages).

Office Action in Japanese Patent Application JP 2017-543596, dated Sep. 20, 2018 (5 pages).

Nishiguchi, I. "Preparation and Reaction of Zinc Compounds in Organic Synthesis," Journal of Synthetic Organic Chemistry, Japan, 37(12), pp. 996-1000 (1979).

* cited by examiner

METHOD FOR PRODUCING OPTICALLY ACTIVE 2-(2-FLUOROBIPHENYL-4-YL) PROPANOIC ACID

CROSS-REFERENCE TO RELATED PATENT APPLICATIONS

This application is a National Stage Entry of International Application No. PCT/JP2016/078939, filed Sep. 29, 2016, which claims priority from Japanese Patent Application No. 2015-194284, filed Sep. 30, 2015. The entire contents of the above-referenced applications are expressly incorporated herein by reference.

TECHNICAL FIELD

The present invention relates to a novel process for producing optically active 2-(2-fluorobiphenyl-4-yl)propanoic acid.

BACKGROUND ART

It is known that 2-(2-fluorobiphenyl-4-yl)propanoic acid or pharmaceutically acceptable salts thereof which have anti-inflammatory action, analgesic action and so forth find extensive use as drugs. Processes so far reported for the production of 2-(2-fluorobiphenyl-4-yl)propanoic acid include, for example, a method of obtaining the same using 2-(2-fluorobiphenyl-4-yl)magnesium bromide and a metal salt of 2-bromopropionic acid (Patent Literature 1) and a method of obtaining the same from an ester intermediate prepared using 2-(2-fluorobiphenyl-4-yl)magnesium bromide, a 2-bromopropionic acid ester, and a nickel catalyst (Patent Literature 2). However, each of these methods ends up with synthesis of a racemate and to obtain optically active 2-(2-fluorobiphenyl-4-yl)propanoic acid, it is further required to perform subsequent optical resolution. A method so far reported for optical resolution is by forming a salt with, for example, an optically active amine so that a salt of one of the two optical isomers is allowed to crystallize preferentially but to obtain 2-(2-fluorobiphenyl-4-yl)propanoic acid of high optical purity, more than one recrystallization step is essential, with the recovery being as low as about 60% (Patent Literature 3). In addition, a method so far reported for asymmetric synthesis is by asymmetric hydrogenation of 2-(2-fluorobiphenyl-4-yl)acrylic acid (Non-Patent Literature 1) but this is not a practical approach because not only does it involve a lot of steps but at the same time a toxic rhodium catalyst is used in the final step.

As techniques for constructing a carbon-carbon bond stereospecifically at α-position of carbonyl, Non-Patent Literature 2 reports asymmetric Kumada reaction that uses a nickel catalyst and an optically active bisoxazoline ligand on the substrate α-haloketone whereas Non-Patent Literature 3 and Non-Patent Literature 4 report asymmetric Negishi reaction in which α-haloamide and α-haloketone are respectively used as a substrate. However, asymmetric Kumada reaction requires low reaction temperatures ranging from −60 to −40° C.; in addition, neither asymmetric Kumada nor Negishi reaction is suitable for use in industrial-scale production because both reactions use 6.5 to 13% of an optically active bisoxazoline ligand as obtained by multi-stage synthesis, and there are no reports made on the synthesis of profens, nor on the synthesis using as a substrate, α-haloesters that can be easily derived to profens. As regards the construction of profen structures, asymmetric Kumada reaction that uses a cobalt catalyst and an optically active bisoxazoline ligand has been reported in Patent Literature 4, Patent Literature 5 and Non-Patent Literature 5, and asymmetric Kumada reaction using an iron catalyst and an optically active bisoxazoline ligand has been reported in Non-Patent Literature 6. However, none of these approaches are suitable for use in industrial-scale production because asymmetric Kumada reaction using a cobalt catalyst involves the very low reaction temperature condition of −80° C. and, further in addition, each of the reactions mentioned above uses 6 to 12% of the optically active bisoxazoline ligand.

Hence, it has been desired to develop a process suitable for industrial-scale production of optically active 2-(2-fluorobiphenyl-4-yl)propanoic acid.

CITATION LIST

Patent Literature

PTL 1: U.S. Pat. No. 3,959,364A
PTL 2: JP 2004-339085A
PTL 3: JP 2000-143580A
PTL 4: CN103755554
PTL 5: CN103755566

Non-Patent Literature

NPTL 1: Org. Chem. Front., 2014, 1, 155.
NPTL 2: J. Am. Chem. Soc., 2010, 132, 1264.
NPTL 3: J. Am. Chem. Soc., 2005, 127, 4594.
NPTL 4: Angew. Chem. Int. Ed., 2009, 48, 154.
NPTL 5: J. Am. Chem. Soc., 2014, 136, 17662.
NPTL 6: J. Am. Chem. Soc., 2015, 137, 7128.

SUMMARY OF INVENTION

Technical Problem

An object of the invention is to provide a novel process for producing optically active 2-(2-fluorobiphenyl-4-yl)propanoic acid.

Solution to Problem

The present inventors repeated intensive studies with a view to attaining the above-stated object and as a result they found the following: when a compound represented by formula [1] (hereinafter sometimes referred to as compound [1]) was reacted with magnesium, optionally further with a zinc compound, to prepare an organometallic reagent, which was reacted with a compound represented by formula [2] (hereinafter sometimes referred to as compound [2]) in the presence of a catalytic amount of a nickel compound and a catalytic amount of an optically active compound represented by formula [3] (hereinafter sometimes referred to as compound [3]) to obtain a compound represented by formula [4] (hereinafter sometimes referred to as compound [4]) which was subsequently converted to a compound represented by formula [5] (hereinafter sometimes referred to as compound [5]) or a pharmaceutically acceptable salt thereof, whereby optically active 2-(2-fluorobiphenyl-4-yl) propanoic acid could be produced.

SCHEME 1

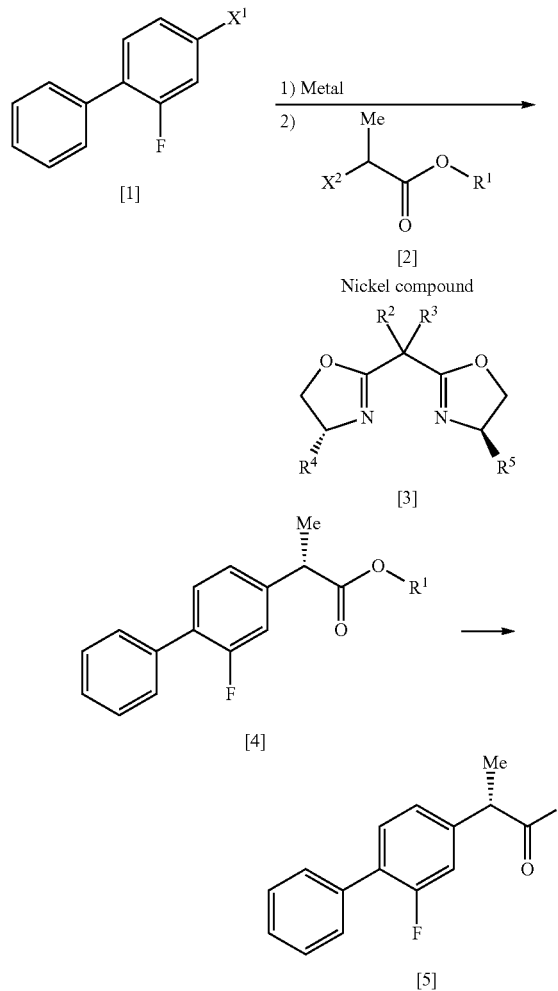

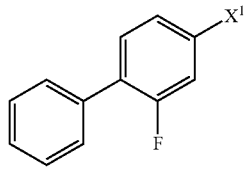

(b) a step of reacting a compound of formula [2] with the organometallic reagent prepared in step (a) in the presence of a catalytic amount of a nickel compound and a catalytic amount of an optically active compound of formula [3] to obtain a compound of formula [4]; and

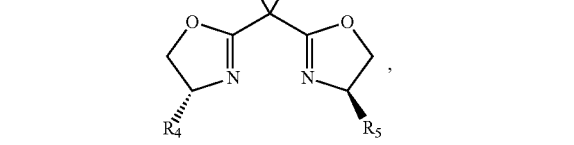

(c) a step of converting the obtained compound of formula [4] to a compound of formula [5] or a pharmaceutically acceptable salt thereof;

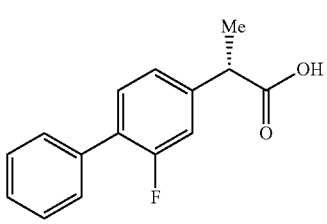

The present inventors also found that according to the above-described production process, the compound of formula [4] could be produced by reacting the compound of formula [2] with the prepared organometallic reagent in the presence of a smaller catalytic amount of the nickel compound and a smaller catalytic amount of the optically active compound of formula [3] than in the conventional methods.

The present inventors further found that according to the above-described production process, the compound of formula [4] could be produced by reacting the compound of formula [2] with the prepared organometallic catalyst at a higher reaction temperature in the presence of a catalytic amount of the nickel compound and a catalytic amount of the optically active compound of formula [3] than in the conventional methods.

Briefly, the present invention relates to the following.
(1) A process for producing optically active 2-(2-fluorobiphenyl-4-yl)propanoic acid or a pharmaceutically acceptable salt thereof, which comprises the following steps (a)-(c):
(a) a step of preparing an organometallic reagent which comprises reacting a compound of formula [1] with magnesium;

provided that in the compounds of above formulas [1] to [5] in foregoing steps (a)-(c):
$X^1$ represents a halogen atom;
$X^2$ represents a halogen atom;
$R^1$ represents tert-butyldiphenylsilyl, $C_{1-6}$ alkyl, $C_{2-6}$ alkenyl, $C_{3-8}$ cycloalkyl, phenyl, or benzyl optionally substituted with one or two groups selected from group A1 of substituents;

$R^2$ and $R^3$ independently represent $C_{1-6}$ alkyl, or $R^2$, $R^3$ and the carbon atom adjacent to said substituents may, taken together, form $C_{3-6}$ cycloalkane;

$R^4$ and $R^5$ independently represent $C_{1-6}$ alkyl, benzyl, phenethyl, or phenyl optionally substituted with one or two groups selected from group A2 of substituents, where group A1 of substituents represents a group consisting of $C_{1-6}$ alkyl and phenyl, and group A2 of substituents represents a group consisting of a halogen atom, $C_{1-6}$ alkyl, halo-$C_{1-6}$ alkyl, $C_{1-6}$ alkoxy, halo $C_{1-6}$alkoxy, and phenyl.

(2) A process as recited in (1), wherein in step (a), the compound of formula [1], after being reacted with magnesium, is further reacted with zinc chloride or zinc bromide to prepare the organometallic reagent.

(3) A process as recited in (1) or (2), wherein the compound of formula [2] in step (b) is such that $R^1$ is $C_{1-6}$ alkyl.

(4) A process as recited in (3), wherein the compound of formula [2] in step (b) is so a $R^1$ is tert-butyl.

(5) A process as recited in any one of (2)-(4), wherein relative to the compound of formula [2], the catalytic amount of the nickel compound used in step (b) is from 0.03 to 1.00 mol % and the catalytic amount of the optically active compound of formula [3] which is used in step (b) is from 0.036 to 1.20 mol %.

(6) A process as recited in (1), (3) or (4), wherein relative to the compound of formula [2], the catalytic amount of the nickel compound used in step (b) is from 0.50 to 1.00 mol % and the catalytic amount of the optically active compound of formula [3] which is used in step (b) is from 0.60 to 1.20 mol %.

(7) A process as recited in any one of (2)-(5), wherein the reaction temperature is from 0 to 25° C. in step (b).

(8) A process as recited in (1), (3), (4) or (6), wherein the reaction temperature is from −20 to 0° C. in step (b).

(9) A process as recited in any one of (1)-(8), wherein the step of converting the compound of formula [4] to the compound of formula [5] in step (c) is by conversion under acidic conditions.

(10) A process as recited in any one of (1)-(9), wherein the optically active compound of formula [3] in step (b) is such that $R^2$ and $R^3$ are both methyl, and $R^4$ and $R^5$ are both phenyl.

(11) A process as recited in any one of (2)-(5) and (7)-(9), wherein in step (a), the molar ratio between the organomagnesium reagent prepared by reacting the compound of formula [1] with magnesium and the zinc chloride or zinc bromide which is further reacted with the reagent is from 2:1 to 3:1.

(12) A process as recited in (2), wherein relative to the compound of formula [2], the catalytic amount of the nickel compound used in step (b) is 0.10 mol % or less, and the catalytic amount of the optically active compound of formula [3] which is used in step (b) is 0.12 mol % or less.

(13) A process as recited in (1), wherein relative to the compound of formula [2], the catalytic amount of the nickel compound used in step (b) is 1.00 mol % or less, and the catalytic amount of the optically active compound formula [3] which is used in step (b) is 1.20 mol % or less.

(14) A process as recited in (9), wherein the acid used in step (c) for conversion to the compound of formula [5] under acidic conditions is an acid selected from the group consisting of hydrochloric acid, sulfuric acid, formic acid, trifluoroacetic acid, methanesulfonic acid, and p-toluenesulfonic acid.

(15) A process as recited in (2), wherein relative to the compound of formula [2], the catalytic amount of the nickel compound used in step (b) is 1.00 mol % or less, and the catalytic amount of the optically active compound formula [3] which is used in step (b) is 1.20 mol % or less.

(16) A process as recited in (15), wherein the reaction temperature is 0° C. or above in step (b).

(17) A process for producing optically active 2-(2-fluorobiphenyl-4-yl)propanoic acid or a pharmaceutically acceptable salt thereof, which consists of the following steps (a)-(c):

(a) a step of preparing an organometallic reagent which comprises reacting a compound of formula [1] with magnesium and optionally further reacting with zinc chloride or zinc bromide;

[Formula 5]

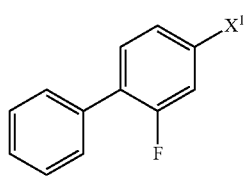

(b) a step of reacting a compound of formula [2] with the organometallic reagent prepared in step (a) in the presence of a catalytic amount of a nickel compound and a catalytic amount of an optically active compound of formula [3] to obtain a compound of formula [4]; and

[Formula 6]

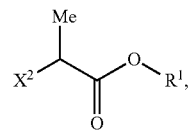

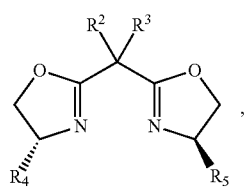

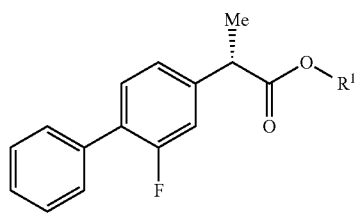

(c) a step of converting the obtained compound of formula [4] to a compound of formula [5] or a pharmaceutically acceptable salt thereof;

[Formula 7]

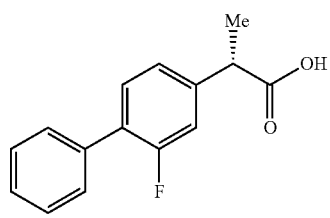

[5]

wherein in above formulas [1] to [5]:
$X^1$ represents a halogen atom;
$X^2$ represents a halogen atom;
$R^1$ represents tert-butyldiphenylsilyl, $C_{1-6}$ alkyl, $C_{2-6}$ alkenyl, $C_{3-8}$ cycloalkyl, phenyl, or benzyl optionally substituted with one or two groups selected from group A1 of substituents;
$R^2$ and $R^3$ independently represent $C_{1-6}$ alkyl, or $R^2$, $R^3$ and the carbon atom adjacent to said substituents may, taken together, form $C_{3-6}$ cycloalkane;
$R^4$ and $R^5$ independently represent $C_{1-6}$alkyl, benzyl, phenethyl, or phenyl optionally substituted with one or two groups selected from group A2 of substituents, where group A1 of substituents represents a group consisting of $C_{1-6}$ alkyl and phenyl, and group A2 of substituents represents a group consisting of a halogen atom, $C_{1-6}$ alkyl, halo-$C_{1-6}$ alkyl, $C_{1-6}$ alkoxy, halo-$C_{1-6}$ alkoxy, and phenyl.
(18) A process as recited in (17), wherein in step (a), the compound of formula [1], after being reacted with magnesium, is further reacted with zinc chloride or zinc bromide.
(19) A process as recited in (17), wherein in step (a), the compound of [1], after being reacted with magnesium, is not reacted with zinc chloride or zinc bromide.
(20) A process as recited in (17), wherein the compound of formula [2] in step (b) is such that $R^1$ is $C_{1-6}$ alkyl.
(21) A process as recited in (17), wherein relative to the compound of formula [2], the catalytic amount of the nickel compound used in step (b) is 1.00 mol % or less and the catalytic amount of the optically active compound of formula [3] which is used in step (b) is 1.20 mol % or less.
(22) A process as recited in (21), wherein the reaction temperature is 0° C. or above in step (b).
(23) A process as recited in (17), wherein the step of converting the compound of formula [4] to the compound of formula [5] in step (c) is by conversion under acidic conditions.
(24) A process as recited in (17), wherein the optically active compound of formula [3] in step (b) is such that $R^2$ and $R^3$ are both methyl, and $R^4$ and $R^5$ are both phenyl.
(25) A process as recited in (20), wherein the compound of formula [2] in step (b) is such that $R^1$ is tert-butyl.
(26) A process as recited in (18), wherein in step (a), the molar ratio between the organomagnesium reagent prepared by reacting the compound of formula [1] with magnesium and the zinc chloride or zinc bromide which is further reacted with the reagent is from 2:1 to 3:1.
(27) A process as recited in (18), wherein relative to the compound of formula [2], the catalytic amount of the nickel compound used in step (b) is 0.10 mol % or less, and the catalytic amount of the optically active compound of formula [3] which is used in step (b) is 0.12 mol % or less.
(28) A process as recited in (27), wherein relative to the compound represented by formula [2], the catalytic amount of the nickel compound used in step (b) is from 0.03 to 0.10 mol % and the catalytic amount of the optically active compound formula [3] which is used in step (b) is from 0.036 to 0.12 mol %.
(29) A process as recited in (19), wherein relative to the compound of formula [2], the catalytic amount of the nickel compound used in step (b) is 1.00 mol % or less, and the catalytic amount of the optically active compound formula [3] which is used in step (b) is 1.20 mol % or less.
(30) A process as recited in (29), wherein relative to the compound of formula [2], the catalytic amount of the nickel compound used in step (b) is from 0.50 to 1.00 mol % and the catalytic amount of the optically active compound formula [3] which is used in step (b) is from 0.60 to 1.20 mol %.
(31) A process as recited in (22), wherein the reaction temperature is from 0 to 25° C. in step (b).
(32) A process as recited in (23), wherein the acid used in step (c) for conversion to the compound of formula [5] under acidic conditions is an acid selected from the group consisting of hydrochloric acid, sulfuric acid, formic acid, trifluoroacetic acid, methanesulfonic acid, and p-toluenesulfonic acid.

Advantageous Effects of Invention

According to the present invention, 2-(2-fluorobiphenyl-4-yl)propanoic acid can be produced with high optical purity. In addition, according to the present invention, the compound of formula [4] can be produced using a smaller catalytic amount of the nickel compound and a smaller catalytic amount of the optically active compound of formula [3] than in the conventional methods. Further in addition, according to the present invention, the compound of formula [4] can be produced at higher reaction temperatures than in the conventional methods.

According to the present invention, there can be provided methods useful as industrial processes for producing optically active 2-(2-fluorobiphenyl-4-yl)propanoic acid which is a drug having anti-inflammatory and analgesic actions.

DESCRIPTION OF EMBODIMENTS

On the following pages, the present invention will be described in detail.

The optically active 2-(2-fluorobiphenyl-4-yl)propanoic acid that can be produced by the present invention has the structure depicted below:

[Formula 8]

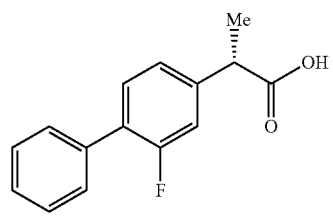

[5]

Hereinafter, unless otherwise noted, the "optically active compound" represented by formulas [4] and [5] refers to either an (S) or (R) form in terms of absolute configuration.

In the present invention, "n" means normal, "i" iso, "s" and "sec" secondary, "t" and "tert" tertiary, "c" cyclo, "o" ortho, "m" meta, and "p" para.

The "halogen atom" is a fluorine atom, a chlorine atom, a bromine atom or an iodine atom.

The term "$C_{1-6}$ alkyl" refers to a straight-chained or branched alkyl having 1 to 6 carbon atoms. Examples include methyl, ethyl, n-propyl, isopropyl, n-butyl, isobutyl, sec-butyl, tart-butyl, n-pentyl, isopentyl, neopentyl, 2-methylbutyl, tert-amyl, n-hexyl, isohexyl, etc.

The term "halo-$C_{1-6}$ alkyl" refers to a straight-chained or branched alkyl having 1 to 6 carbon atoms as substituted by halogen atom(s). The preferred number of halogen substitutions is from one to five, and the preferred halogen atom is a fluorine atom. Examples include monofluoromethyl, difluoromethyl, trifluoromethyl, 1-fluoroethyl, 1,1-difluoroethyl, 1,1,2,2,2-pentafluoroethyl, 2-fluoroethyl, 2-fluoro-2-methylpropyl, 2,2-difluoropropyl, 1-fluoro-2-methylpropan-2-yl, 1,1-difluoro-2-methylpropan-2-yl, 1-fluoropentyl, 1-flourohexyl, etc.

The term "$C_{2-6}$alkenyl" refers to a straight-chained or branched alkenyl having 2 to 6 carbon atoms. Examples include ethenyl, (E)-prop-1-en-1-yl, (Z)-prop-1-en-1-yl, prop-2-en-1-yl, but-3-en-1-yl, pent-4-en-1-yl, hex-5-en-1-yl, etc.

The term "$C_{1-6}$alkoxy" refers to a straight-chained or branched alkoxy having 1 to 6 carbon atoms. Examples include methoxy, ethoxy, n-propoxy, isopropoxy, n-butoxy, isobutoxy, sec-butoxy, tert-butoxy, n-pentyloxy, isopentyloxy, neopentyloxy, 2-methylbutoxy, n-hexyloxy, isohexyloxy, etc.

The term "halo-$C_{1-6}$ alkoxy" refers to a straight-chained or branched alkoxy having 1 to 6 carbon atoms as substituted by halogen atom(s). The preferred number of halogen substitutions is from one to five, and the preferred halogen atom is a fluorine atom. Examples include monofluoromethoxy, difluoromethoxy, trifluoromethoxy, 1-fluoroethoxy, 1,1-difluoroethoxy, 1,1,2,2-tetrafluoroethoxy, 2-fluoroethoxy, 2,2,2-trifluoroethoxy, 3,3,3-trifluoropropoxy, 1,3-difluoropropan-2-yloxy, 2-fluoro-2-methylpropoxy, 2,2-difluoropropoxy, 1-fluoro-2-methylpropan-2-yloxy, 1,1-difluoro-2-methylpropan-2-yloxy, 4,4,4-trifluorobutoxy, etc.

The term "$C_{3-6}$ cycloalkane" means a cycloalkane having 3 to 6 carbon atoms, which is selected from the group consisting of cyclopropane, cyclobutane, cyclopentane, and cyclohexane.

The term "$C_{3-8}$ cycloalkyl" means a cycloalkyl having 3 to 8 carbon atoms, which is selected from the group consisting of cyclopropyl, cyclobutyl, cyclopentyl, cyclohexyl, cycloheptyl, and cyclooctyl.

The "organometallic reagent" is a reagent prepared by reacting an organic compound(s) with a metallic reagent(s) and such organometallic reagent includes a reagent prepared by further reacting the obtained organometallic reagent with another metallic reagent. In the present invention, the organometallic reagent refers to an organomagnesium reagent prepared by reacting an organic compound with magnesium (the reagent is hereinafter sometimes referred to as a Grignard reagent), as well as an organozinc containing reagent prepared by further reaction with a zinc compound (the reagent is hereinafter referred to as an organozinc reagent).

The "zinc compound" may be of any type which, upon reaction with the organomagnesium reagent, can be prepared as the organozinc reagent and it may be exemplified by a zinc halide, specifically by zinc chloride, zinc bromide, or zinc iodide.

The term "nickel compound" refers to a halogen-containing nickel compound or nickel complex and examples include nickel(II) chloride, nickel(II) bromide, nickel(II) iodide, nickel(II) chloride/DME complex (DME: 1,2-dimethoxyethane), nickel(II) acetylacetonate, and nickel(II) bis (triphenylphosphine) chloride.

The "ether-based solvent" may be exemplified by tetrahydrofuran, 1,4-dioxane, methyltetrahydrofuran, diethyl ether, dimethoxyethane, and cyclopentyl methyl ether.

The "benzene-based solvent" may be exemplified by benzene, toluene, and xylene.

The "hydrocarbon-based solvent" may be exemplified by toluene, xylene, benzene, heptane, and hexane.

The "alcoholic solvent" may be exemplified by methanol, ethanol, 1-propanol, 2-propanol, and tert-butyl alcohol.

The "ester-based solvent" may be exemplified by ethyl acetate.

The "pharmaceutically acceptable salt" may be exemplified by amino acid salts such as glycine salt, lysine salt, arginine salt, histidine salt, ornithine salt, glutamic acid salt, and aspartic acid salt; inorganic salts such as lithium salt, sodium salt, potassium salt, calcium salt, and magnesium salt; or salts with organic bases such as ammonium salt, triethylamine salt, diisopropylamine salt, and cyclohexylamine salt.

Note that the salts include hydrous salts.

The optically active compound represented by formula [3] will be described below.

[Formula 9]

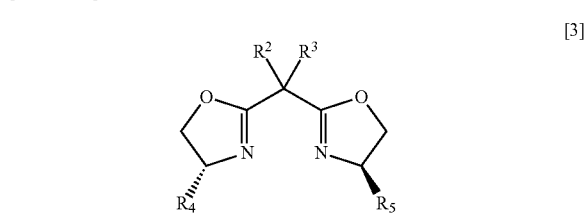

[3]

In accordance with the production process of the present invention, the compound of formula [2] is reacted with the organometallic reagent prepared in step (a) using a catalytic amount of the optically active compound of formula [3] in the presence of a catalytic amount of the nickel compound, whereby the optically active compound of formula [4] can be produced.

In the process, if an optically active compound of formula [3] having an absolute configuration of (R,R) is used, a compound of formula [4] having an absolute configuration of (S) can be produced. Conversely, if an optically active compound of formula [3] having an absolute configuration of (S,S) is used, a compound of formula [4] having an absolute configuration of (R) can be produced.

The optically active compounds of formula [3] are either commercially available or obtainable by known methods described in the literature (for example, J. Am. Chem. Soc., 2014, 136, 17662).

Symbols (R) and (S) are used herein to specify the configurations of chiral molecules having central chirality. Symbols (Z) and (E) are used herein to describe the stereochemistry of a molecule having a double bond: the substituent groups attached to each carbon atom of the double bond in the plane of the molecule are considered and if the groups of higher priority in sequence rules are on opposite sides of the double bond, the molecule is designated (E) and if the higher-priority groups are on the same side, the molecule is designated (Z).

The "catalyst" is a substance that does not change on its own but which acts as an intermediary for other substance to undergo chemical reaction so that the reaction rate is increased or slowed down. In general, the catalyst may be used in an amount less than or equal to the amount of the other substance (or substrate) which undergoes the reaction. In the present invention, the "catalytic amount" means as follows: take, for example, the case where the compound of formula [2] is reacted with the organomagnesium reagent and in this case, relative to the compound of formula [2], the nickel compound is used in an amount of 10 mol % or less, preferably 1.00 mol % or less, more preferably in the range from 0.50 to 1.00 mol %, whereas the optically active compound of formula [3] is 12 mol % or less, preferably 1.20 mol % or less, more preferably in the range from 0.60 to 1.20 mol %; take, for example, the case where the compound of formula [2] is reacted with the organozinc reagent and in this case, relative to the compound of formula [2], the nickel compound is used in an amount of 10 mol % or less, preferably 1.00 mol % or less, more preferably in the range from 0.03 to 1.00 mol %, even more preferably 0.10 mol % or less, and most preferably in the range from 0.03 to 0.10 mol %, whereas the optically active compound of formula [3] is used in an amount of 12 mol % or less, preferably in the range from 0.036 to 1.20 mol %, more preferably 0.12 mol % or less, and even more preferably in the range from 0.036 to 0.12 mol %.

There is no particular upper limit on the amount in which compound [3] is used but if it is used in excess amount relative to the nickel compound, reaction can be allowed to proceed efficiently.

In the case where compound [3] is used as a catalyst, its amount is 12 mol % or less relative to compound [2] and in the case where the compound of formula [2] is reacted with the organomagnesium reagent, it is more preferably used in an amount of 1.20 mol % or less, and even more preferably in an amount ranging from 0.60 to 1.20 mol %; in the case where the compound of formula [2] is reacted with the organozinc reagent, it is more preferably used in an amount of 0.12 mol % or less, and even more preferably in an amount ranging from 0.036 to 0.12 mol %.

There is no particular upper limit on the amount of the nickel compound.

In the case where the nickel compound is used as a catalyst, its amount is 10 mol % or less relative to compound [2] and in the case where the compound of formula [2] is reacted with the organomagnesium reagent, it is more preferably used in an amount of 1.00 mol % or less, and even more preferably in an amount ranging from 0.50 to 1.00 mol %; in the case where the compound of formula [2] is reacted with the organozinc reagent, it is more preferably used in an amount of 0.10 mol % or less, and even more preferably in an amount ranging from 0.03 to 0.10 mol %.

The preferred embodiments of the present invention are as follows.

The preferred $X^1$ is a chlorine atom, a bromine atom, or an iodine atom; the more preferred $X^1$ is a bromine atom.

The preferred $X^2$ is a chlorine atom, a bromine atom, or an iodine atom; the more preferred $X^2$ is a chlorine atom or a bromine atom.

The preferred $R^1$ is tert-butyldiphenylsilyl, $C_{1-6}$ alkyl, $C_{2-6}$ alkenyl, $C_{3-8}$ cycloalkyl, phenyl, or benzyl optionally substituted with one or two groups selected from group A1 of substituents; the more preferred $R^1$ is tert-butyldiphenylsilyl, $C_{1-6}$ alkyl, $C_{3-8}$ cycloalkyl, or benzyl optionally substituted with one or two groups selected from group A1 of substituents; even more preferred $R^1$ is tert-butyldiphenylsilyl, tert-butyl, neopentyl, tert-amyl, cyclohexyl, 1-methyl-1-phenylethyl, or benzhydryl; the most preferred $R^1$ is tert-butyl.

The preferred $R^2$ is $C_{1-6}$alkyl; the more preferred $R^2$ is methyl or ethyl; even more preferred $R^2$ is methyl.

The preferred $R^3$ is $C_{1-6}$ alkyl; the more preferred $R^3$ is methyl or ethyl; even more preferred $R^3$ is methyl.

The preferred $C_{3-6}$ cycloalkane which $R^2$, $R^3$ and the carbon atom adjacent to these substituents together form is cyclopropane.

The preferred $R^4$ is $C_{1-6}$ alkyl or phenyl optionally substituted with one or two groups selected from group A2 of substituents, and the more preferred $R^4$ is phenyl.

The preferred $R^5$ is $C_{1-6}$alkyl or phenyl optionally substituted with one or two groups selected from group A2 of substituents, and the more preferred $R^5$ is phenyl.

The preferred zinc compound with which the organomagnesium reagent (Grignard reagent) obtained by reacting the compound of formula [1] with magnesium is optionally farther reacted is zinc chloride or zinc bromide.

The preferred nickel compound is nickel(II) chloride, nickel(II) iodide, nickel(II) chloride/DME complex, nickel (II) acetylacetonate, or nickel(II) bis(triphenylphosphine) chloride.

A preferred embodiment for producing the compound of formula [4] in the present invention is the production method depicted by the following scheme 2.

SCHEME 2

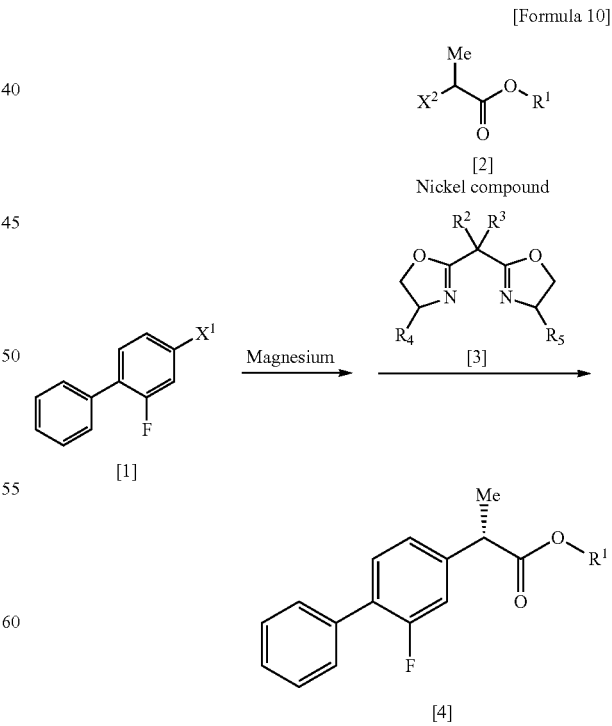

wherein the preferred embodiments of $X^1$, $X^2$, $R^1$, $R^2$, $R^3$, $R^4$, and $R^5$ are as described above.

In this case, the more preferred embodiment is where:
X$^1$ is a bromine atom;
X$^2$ is a chlorine atom or a bromine atom;
R$^1$ is tert-butyl;
R$^2$ and R$^3$ are both methyl; and
R$^4$ and R$^5$ are both phenyl.

Another preferred embodiment for producing the compound of formula [4] in the present invention is the production method depicted by the following scheme 3.

In this case, still another more preferred embodiment is where:
R$^1$ is tert-butyl.

In the production method depicted by the following scheme 4 for converting the obtained compound of formula [4] to the compound of formula [5], a preferred embodiment is conversion under acidic conditions.

SCHEME 3

[Formula 11]

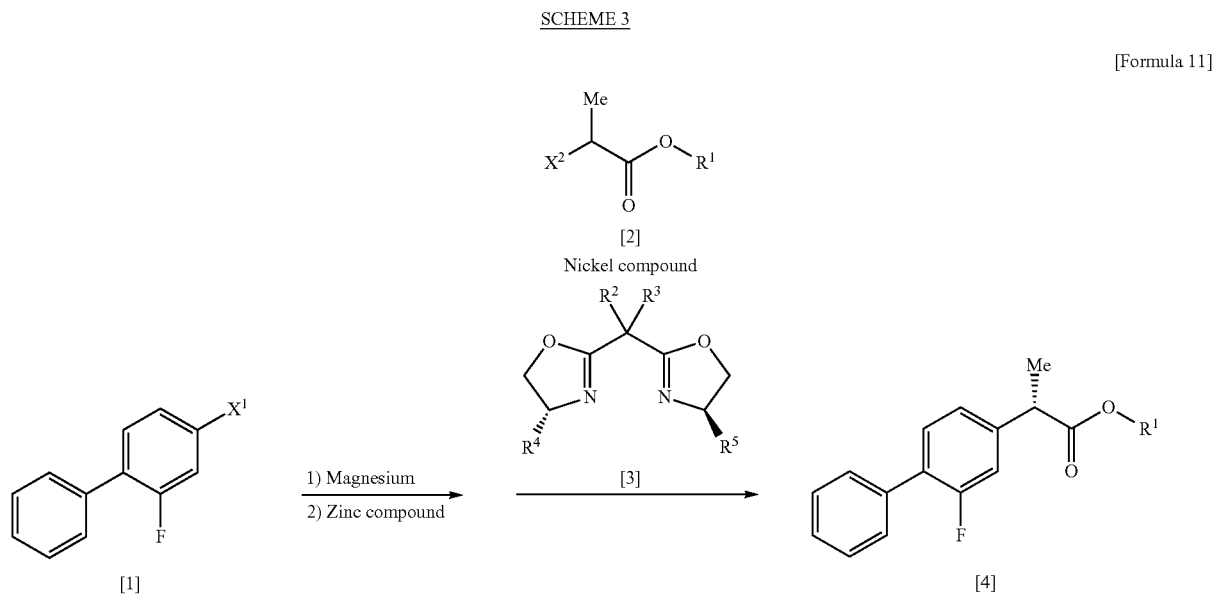

wherein the preferred embodiments of X$^1$, X$^2$, R$^1$, R$^2$, R$^3$, R$^4$, and R$^5$ are as described above. The zinc compound refers to zinc chloride or zinc bromide.

In this case, a more preferred embodiment is where:
X$^1$ is a bromine atom;
X$^2$ is a bromine atom;
R$^1$ is tert-butyldiphenylsilyl, tert-butyl, neopentyl, tert-amyl, cyclohexyl, 1-methyl-1-phenylethyl, or benzhydryl;
R$^2$ and R$^3$ are both methyl or ethyl;
or the C$_{3-6}$ cycloalkane which R$^2$, R$^3$ and the carbon atom adjacent to these substituents together form is cyclopropane;
R$^4$ and R$^5$ are both phenyl; and
the zinc compound is zinc bromide.

In this case, an even more preferred embodiment is where:
R$^2$ and R$^3$ are both methyl.

In this case, a still even more preferred embodiment is where:
R$^1$ is tert-butyl.

Another more preferred embodiment is the following case:
X$^1$ is a bromine atom;
X$^2$ is a bromine atom;
R$^1$ is tert-butyl, tert-amyl, 1-methyl-1-phenylethyl, or benzhydryl;
R$^2$ and R$^3$ are both methyl or ethyl;
or the C$_{3-6}$ cycloalkane which R$^2$, R$^3$ and the carbon atom adjacent to these substituents together form is cyclopropane;
R$^4$ and R$^5$ are both phenyl; and
the zinc compound is zinc bromide.

In this case, an even more preferred embodiment is where:
R$^2$ and R$^3$ are both methyl.

SCHEME 4

[Formula 12]

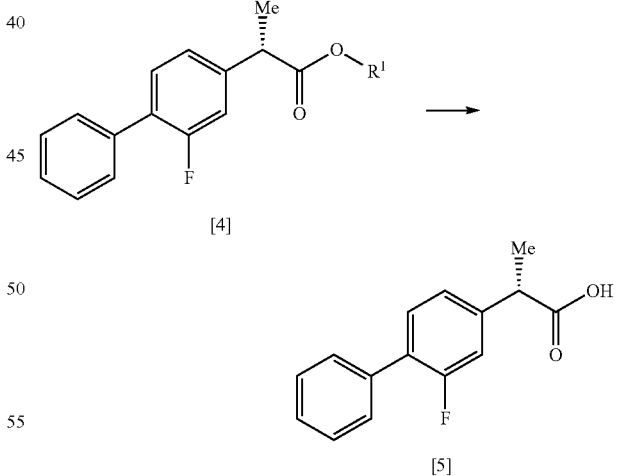

wherein the preferred embodiment of R$^1$ is as described above.

In this case, the more preferred embodiment is where:
R$^1$ is tert-butyl.

In this case, the preferred acid for use in the conversion to the compound of formula [5] is an acid selected from the group consisting of hydrochloric acid, sulfuric acid, formic acid, trifluoroacetic acid, methanesulfonic acid, and p-toluenesulfonic acid, and the more preferred acid is formic acid.

In the next place, the respective steps in the production method of the present invention are explained in detail.
1. Step (a), method of preparing the organomagnesium reagent [6]

SCHEME 5

[Formula 13]

$$\text{[1]} \xrightarrow[\text{Reaction time}]{\substack{\text{Magnesium} \\ \text{Solvent} \\ \text{Reaction temperature}}} \text{Organomagnesium reagent} \\ \text{(Grignard reagent)} \\ \text{[6]}$$

wherein $X^1$ is as previously defined.

Compound [1] to be used in this step may be one in which $X^1$ is a halogen atom. In this case, use of compound [1] in which $X^1$ is a chlorine atom, a bromine atom or an iodine atom is preferred, and use of compound [1] in which $X^1$ is a bromine atom is more preferred.

Magnesium theoretically suffices to be used in an equimolar amount relative to compound [1] but its use may range from about 1.0 to 1.3 equivalents.

Any solvent can be used in this step as long as it does not inhibit the progress of the reaction on its own. Preferred solvents are ether-based; more preferred solvents are tetrahydrofuran, 1,4-dioxane, methyltetrahydrofuran, and diethyl ether; a even more preferred solvent is tetrahydrofuran.

The reaction temperature is preferably so adjusted as to fall between 0 to 60° C. and if necessary, cooling or heating may be performed. In preparing the Grignard reagent, additives such as iodine and 1,2-dibromoethane may be used.

While the reaction time may be determined by checking how much of compound [1] as the starting material remains, it can usually be adjusted to range from half an hour to no more than 10 hours after the addition of compound [1]. It preferably ranges from 2 to 3 hours.

2. Step (b), method of producing the compound of formula [4] from the organomagnesium reagent [6]

SCHEME 6

[Formula 14]

-continued wherein $X^2$, $R^1$, $R^2$, $R^3$, $R^4$, and $R^5$ are as previously defined.

Compound [2] to be used in this step may be one in which $X^2$ is a halogen atom. In this case, use of compound [2] in which $X^2$ is a chlorine atom or a bromine atom is preferred, and use of compound [2] in which $X^2$ is a bromine atom is more preferred. It is also possible to use compound [2] in which $R^1$ is $C_{1-6}$ alkyl. In this case, use of compound [2] in which $R^1$ is tert-butyl is preferred.

The Grignard reagent which is caused to react with compound [2] is used in such a way that compound [1] as the starting material is used in an amount that preferably ranges from 1.0 to 1.5 equivalents relative to compound [2].

Compound [3] to be used in this step may be one in which $R^2$ and $R^3$ are independently $C_{1-6}$ alkyl. In this case, use of compound [3] in which $R^2$ and $R^3$ are both methyl is preferred.

It is also possible to use compound [3] in which $R^4$ and $R^5$ are independently $C_{1-6}$ alkyl, benzyl, phenethyl, or phenyl optionally substituted with one or two groups selected from group A2 of substituents. In this case, use of compound [3] in which $R^4$ and $R^5$ are both phenyl is preferred.

There is no particular upper limit on the amount in which compound [3] is used but if it is used in excess amount relative to the nickel compound, reaction can be allowed to proceed efficiently.

In the case where compound [3] is used as a catalyst, its amount is 12 mol % or less, more preferably 1.20 mol % or less, and even more preferably from 0.60 to 1.20 mol %, relative to compound [2].

There is no particular upper limit on the amount of the nickel compound but if it is 0.5 mol % or more relative to compound [2], reaction can be allowed to proceed efficiently.

In the case where the nickel compound is used as a catalyst, its amount is 10 mol % or less, more preferably 1.00 mol % or less, and even more preferably from 0.50 to 1.00 mol %, relative to compound [2].

As nickel compounds to be used, known nickel catalysts are typically mentioned, including nickel(II) chloride/DME complex, nickel(II) chloride, nickel(II) bis(triphenylphosphine) chloride, nickel(II) iodide, nickel(II) acetylacetonate, etc.; nickel(II) chloride/DME complex and nickel(II) acetylacetonate are more preferred, with nickel(II) acetylacetonate being further preferred.

Any solvent can be used in this step as long as it does not block the progress of the reaction on its own. Preferred solvents are ether-based and benzene-based; a more preferred solvent is tetrahydrofuran.

Solvents may be used either alone or in admixture of two or more types. The amount of their use is usually influenced by the compounds used in the reactions as well as by the properties of the reagents, so it can be set at any values depending on the types of compounds. Preferably, the concentration of compound [2] ranges from 0.05 to 1 M, more preferably from 0.1 to 0.5 M.

The reaction temperature is feasible at anywhere between −78° C. and the boiling point of the reaction solvent but it is preferably selected at between −20° C. to room temperature, more preferably between −20° C. to 0° C., and even more preferably at 0° C.

While the reaction time may be determined by checking how much of the compound [2] remains, it can usually be adjusted to range from half an hour to no more than 24 hours after the addition of the organomagnesium reagent [6].

Compound [4] obtained by the coupling reaction between the organomagnesium reagent [6] and the compound [2] is an (S) form in admixture with an (R) form.

After dissolving the compound [4] in a specified organic solvent under heating, the solution is left to cool until the dissolved compound crystallizes out; the crystal is then filtered, centrifuged or otherwise separated from the solvent; thereafter, the crystal is dried to yield compound [4] in crystal form. Although the process of recrystallization may be performed two or more times, it is usually carried out only once.

The cooling time is not particularly limited but it typically ranges from 10 minutes to 24 hours, preferably from 1 to 5 hours.

Solvents that can be used to recrystallize compound [4] are alcoholic solvents and water; preferred solvents are methanol, ethanol, 2-propanol, and water, with ethanol and water being more preferred.

For crystallization, a seed crystal of compound [4] may be employed depending on the need.

The seed crystal may be obtained by a method well known to the skilled artisan, such as, for example, rubbing the sidewall of a container of the crystallizing solution with a spatula.

Unless specifically noted, the process of crystallization performed at temperatures in the range from −20° C. to 60° C.

By conducting recrystallization in this step, compound [4] as an (S) form can be obtained with high optical purity. Alternatively, recrystallization is not conducted in this step but conversion to compound [5] or a pharmaceutically acceptable salt thereof is first performed, then followed by recrystallization; this process also enables producing compound [5] as an (S) form with high optical purity.

3. Step (a), method of preparing the organozinc reagent [7]

Magnesium theoretically suffices to be used in an equimolar amount but its use may range from about 1.0 to 1.3 equivalents relative to compound [1]. While zinc bromide and zinc chloride May be used as the zinc compound, zinc bromide is preferred. While the zinc compound can be used in 0.3 equivalents to 1.0 equivalent relative to compound [1], it is preferably used in 0.3 equivalents to 0.5 equivalents. More preferably in 0.5 equivalents.

Any solvent can be used in this step as long as it does not block the progress of the reaction on its own. Preferred solvents are ether-based; more preferred solvents are tetrahydrofuran, 1,4-dioxane, 2-methyltetrahydrofuran, and diethyl ether; an even more preferred solvent is tetrahydrofuran.

Solvents may be used either alone or in admixture of two or more types. The amount of their use is usually influenced by the properties of the compounds and the reagents used in the reactions, so it can be set at any values depending on the types of compounds. Preferably, the concentration of compound [2] ranges from 0.05 to 1 M, more preferably from 0.1 to 0.5 M.

The reaction temperature is preferably so adjusted as to fall between 0 to 60° C. and if necessary, cooling or heating may be performed. In preparing the Grignard reagent, additives such as iodine and 1,2-dibromoethane may be used.

For the preparation of the Grignard reagent, the reaction time may be determined by checking how ranch of compound [1] as the starting material remains and it can usually be adjusted to range from half an hour to no more than 10 hours after the addition of compound [1]. Preferably, the reaction time ranges from 2 to 3 hours. For the preparation of the organozinc reagent, the reaction time is preferably from 10 minutes to an hour after adding zinc bromide or zinc chloride to the Grignard reagent.

4. Step (b), method of producing the compound [4] from the organozinc reagent [7]

SCHEME 7

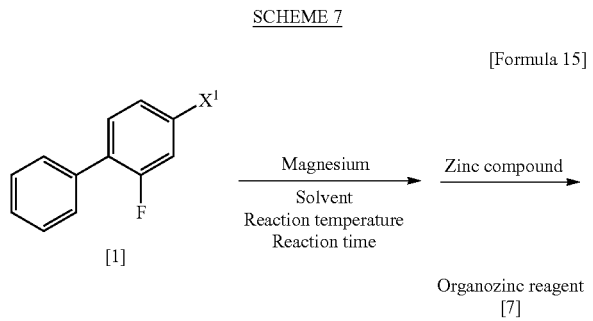

[Formula 15]

wherein $X^1$ and the zinc compound are as previously defined.

Compound [1] to be used in this step may be one in which $X^1$ is a halogen atom. In this case, use of compound [1] in which $X^1$ is a chlorine atom, a bromine atom or an iodine atom is preferred, and use of compound [1] in which $X^1$ is a bromine atom is more preferred.

SCHEME 8

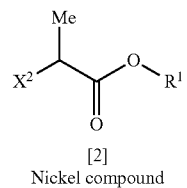

[Formula 16]

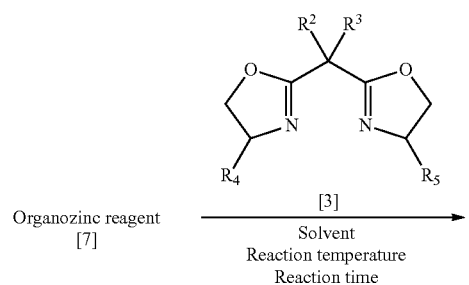

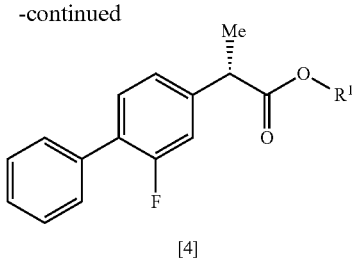

[4]

wherein $X^2$, $R^1$, $R^2$, $R^3$, $R^4$, and $R^5$ are as previously defined.

Compound [2] to be used in this step may be one in which $X^2$ is a halogen atom. In this case, use of compound [2] in which $X^2$ is a bromine atom is preferred. It is also possible to use compound [2] in which $R^1$ is tert-butyldiphenylsilyl, $C_{1-6}$ alkyl, $C_{2-6}$ alkenyl, $C_{3-8}$ cycloalkyl, phenyl, or benzyl optionally substituted with one or two groups selected from group A1 of substituents. In this case, use of compound [2] in which $R^1$ is tert-butyldiphenylsilyl, $C_{1-6}$ alkyl, $C_{3-8}$ cycloalkyl, or benzyl optionally substituted with one or two groups selected from group A1 of substituents is preferred; use of compound [2] in which $R^1$ is tert-butyldiphenylsilyl, tert-butyl, neopentyl, tert-amyl, cyclohexyl, 1-methyl-1-phenylethyl, or benzhydryl is more preferred; and use of compound [2] in which $R^1$ is tert-butyl is even more preferred.

The organozinc reagent which is caused to react with compound [2] is used in such a way that the starting material compound [1] is preferably used in an amount ranging from 1.0 to 1.5 equivalents relative to compound [2].

Compound [3] to be used in this step may be one in which $R^2$ and $R^3$ are independently $C_{1-6}$ alkyl. In this case, use of compound [3] in which $R^2$ and $R^3$ are both methyl or ethyl is preferred, and use of compound [3] in which $R^2$ and $R^3$ are both methyl is more preferred.

It is also possible to use compound [3] in which $R^2$, $R^3$, and the carbon atom adjacent thereto together form $C_{3-6}$ cycloalkane. In this case, use of compound [3] in which $R^2$, $R^3$, and the carbon atom adjacent thereto together form cyclopropane is preferred.

it is also possible to use compound [3] in which $R^4$ and $R^5$ are independently $C_{1-6}$ alkyl, benzyl, phenethyl, or phenyl optionally substituted with one or two groups selected from group A2 of substituents. In this case, use of compound [3] in which $R^4$ and $R^5$ are both phenyl is preferred.

There is no particular upper limit on the amount in which compound [3] is used but if it is used in excess amount relative to the nickel compound, reaction can be allowed to proceed efficiently.

In the case where compound [3] is used as a catalyst, its amount is 12 mol % or less, preferably in the range from 0.036 to 1.20 mol %, more preferably 0.12 mol % or less, and even more preferably from 0.036 to 0.12 mol %, relative to compound [2].

There is no particular upper limit on the amount of the nickel compound.

In the case where the nickel compound is used as a catalyst, its amount is 10 mol % or less, preferably in the range from 0.03 to 1.00 mol %, more preferably 0.10 mol % or less, and even more preferably from 0.03 to 0.10 mol %, relative to compound [2].

As nickel compounds to be used, known nickel catalysts are mentioned, including nickel(II) chloride/DME complex, nickel(II) chloride, nickel(II) bis(triphenylphosphine) chloride, nickel(II) iodide, nickel(II) acetylacetonate, etc.

Any solvent can be used in this step as long as it does not block the progress of the reaction on its own. Preferred solvents are ether-based, benzene-based, and ester-based; more preferred solvents are tetrahydrofuran, 1,4-dioxane, 2-methyltetrahydrofuran, toluene, and ethyl acetate; an even more preferred solvent is tetrahydrofuran.

Solvents may be used either alone or in admixture of two or more types. The amount of their use is usually influenced by the properties of the compounds and the reagents used in the reactions, so it can be set at any values depending on the types of compounds. Preferably, the concentration of compound [2] ranges from 0.05 to 1 M, more preferably from 0.1 to 0.5 M.

in the case of using additives, they may be used either alone or in admixture of two or more types. The amount of an additive, if used at all, can be set any values depending on the types of the compounds used in the reactions and it is from 0.1 to 50 equivalents, preferably from 0.5 to 20 equivalents, and more preferably from 1 to 5 equivalents, relative to compound [1].

The reaction temperature is feasible at anywhere between −78° C. and the boiling point of the reaction solvent but it is preferably selected at between −20 to 25° C., more preferably between 0 to 25° C.

While the reaction time may be determined by checking how much of the starting material compound remains, it can usually be adjusted to range from half an hour to no more than 24 hours after the addition of the organozinc reagent [7].

Compound [4] obtained by the coupling reaction between the organozinc reagent [7] and the compound [2] is an (S) form in admixture with an (R) form.

As previously mentioned, by conducting recrystallization in this step, compound [4] as an (S) form can be obtained with high optical purity. Alternatively, recrystallization is not conducted in this step but conversion to compound [5] or a pharmaceutically acceptable salt thereof is first performed, then followed by recrystallization; this process also enables producing compound [5] as an (S) form with high optical purity.

5. Step (c), method of producing the compound of formula [5]

SCHEME 9

[Formula 17]

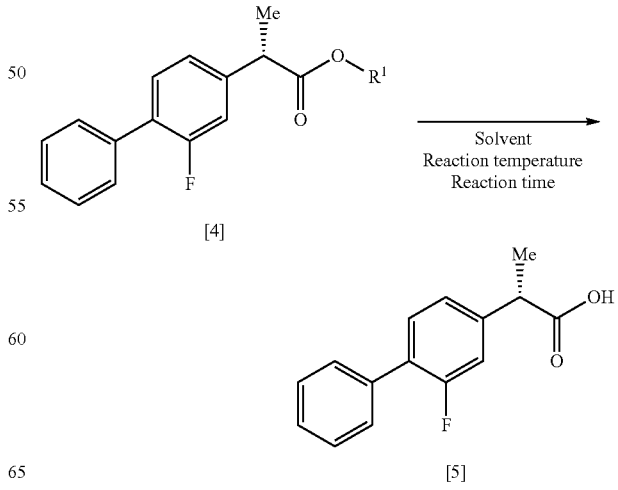

wherein R¹ is as previously defined.

While the preferred is as previously mentioned, the more preferred R¹ is tert-butyl.

For this deprotection step, commonly known conditions may be employed (see Theodora W. Greene, Peter. G. M. Wuts; Greene's Protective Groups in Organic Synthesis, Fourth Edition, Wiley-Interscience).

In this step, the conversion to compound [5] may be performed under acidic conditions.

The acid that can be used is hydrochloric acid, sulfuric acid, formic acid, acetic acid, trifluoroacetic acid, phosphoric acid, methanesulfonic acid, or p-toluenesulfonic acid. Use of hydrochloric acid, sulfuric acid, formic acid, trifluoroacetic acid, methanesulfonic acid, or p-toluenesulfonic acid is preferred, and use of formic acid is more preferred.

Any solvent can be used in this step as long as it does not block the progress of the reaction. Preferred solvents are heptane, toluene, acetic acid, and 1,4-dioxane.

The reaction temperature is feasible at anywhere between room temperature and the boiling point of the reaction solvent but it is preferably selected at between room temperature and 80° C.

While the reaction time may be determined by checking how much of compound [4] as the starting material remains, it can usually be adjusted to range from half an hour to no more than 40 hours.

After dissolving the compound [5] in a specified organic solvent under heating, the solution is left to cool until the dissolved compound crystallizes out; the crystal is then filtered, centrifuged or otherwise separated from the solvent; thereafter, the crystal is dried to yield compound [5] in crystal form. Although the process of recrystallization may be performed two or more times, it is usually carried out only once.

The cooling time is not particularly limited but it typically ranges from 10 minutes to 24 hours, preferably from 1 to 5 hours.

Solvents that can be used to recrystallize compound [5] are benzene-based solvents, hydrocarbon-based solvents, alcoholic solvents, and water; preferred solvents are toluene, heptane, methanol, ethanol, 2-propanol, and water, with toluene and heptane being more preferred.

In the present process of recrystallization, solvents may be used either alone or in admixture of two or more types.

For crystallization, a seed crystal of compound [5] may be employed depending on the need.

The seed crystal may be obtained by a method well known to the skilled artisan, such as, for example, rubbing the sidewall of a container of the crystallizing solution with a spatula.

The seed crystal of compound [5] can also be obtained by the method described in Example 9-1 to be set out later.

Unless otherwise noted, crystallization is performed at temperatures in the range from −20° C. to 80° C.

The compounds obtained by the production methods described above may be purified by known means such as, for example, recrystallization and various chromatographic techniques, whereupon the end products can be obtained.

EXAMPLES

The present invention is explained in greater detail by means of the following Examples which are by no means intended to limit the present invention and may be modified without departing from the scope of the present invention.

In the following Examples, silica gel column chromatography was performed using packed columns (Reveleris (registered trademark) Flash Cartridges Silica manufactured by Grace, and Biotage (registered trademark) SNAP Cartridge HP-Sphere manufactured by Biotage).

The phase separator used in the following Examples was ISOLUTE (registered trademark) Phase Separator manufactured by Biotage.

Nuclear magnetic resonance (NMR) spectra were measured at 600 MHz (JNM-ECA 600, JEOL) and 400 MHz (AVANCE III-HD400, BRUKER) at room temperature. The chemical shift data presented herein are expressed in parts per million (δ) relative to tetramethylsilane as an internal standard substance.

Mass spectra were measured with a mass spectrometer, LCMS-IT-TOF of Shimadzu (ESI/APCI dual type: ESI=electrospray ionization; APCI=atmospheric pressure chemical ionization).

Optical purity was measured by high-performance liquid chromatography (HPLC) using Agilent 1100 manufactured by Agilent Technology, and supercritical fluid chromatography (SFC) using Acquity UPC2 manufactured by Waters.

Optical rotation was conducted with a polarimeter, AUTOPOL V manufactured by Rudolph Research Analytical.

The abbreviations used herein have the following meanings.

s: singlet
d: doublet
t: triplet
q: quartet
m: multiplet
J: coupling constant
Hz: Hertz
CHLOROFORM-d, $CDCl_3$: deuterated chloroform
NMR: nuclear magnetic resonance
MS: mass spectrum
ee: enantiometric excess
HPLC: high-performance liquid chromatography
Et: ethyl
Me: methyl
Ph: phenyl
MsOH: mesylic acid, methanesulfonic acid
TsOH: tosylic acid, p-toluenesulfonic acid
TFA: trifluoroacetic acid
acac: acetylacetonate
$PPh_3$: triphenylphosphine
TBDPS: tert-butyldiphenylsilyl
THF: tetrahydrofuran
DME: 1,2-dimethoxyethane
$MgSO_4$: anhydrous magnesium sulfate
rt: room temperature For the nomenclature of compounds, software such as ACD/Name (ACD/Labs 12.01, Advanced Chemistry Development Inc.) was sometimes used.

As used herein, the term "room temperature" refers to between 20 and 30° C.

The term "ice cooling" refers to between 0 and 5° C.

Example 1-1

Method of producing tert-butyl(S)-2-(2-fluorobiphenyl-4-yl)propanoate

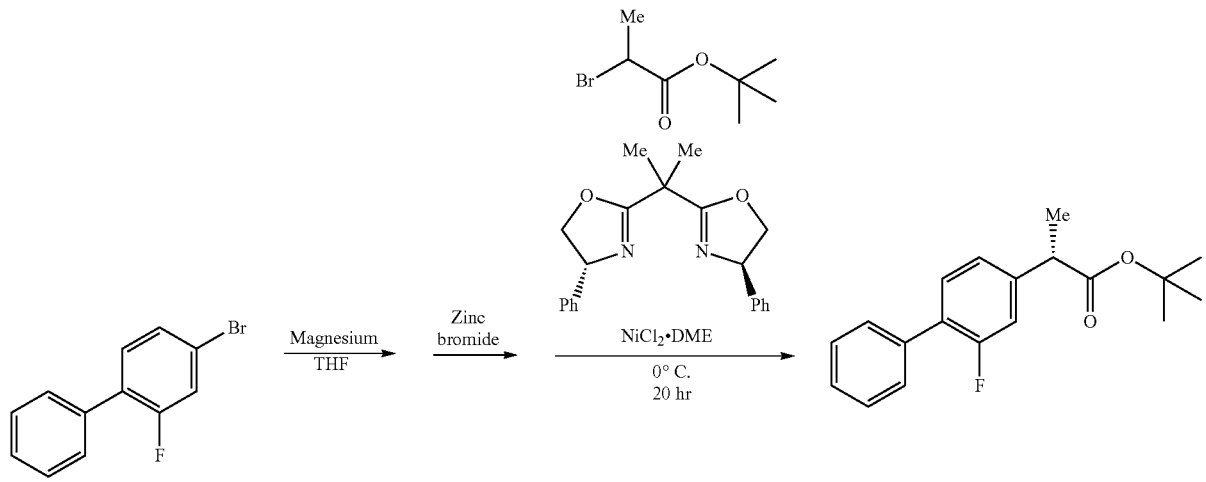

[Formula 18]

(1) In an argon atmosphere, a solution of 4-bromo-2-fluorobiphenyl (1.00 g, 3.98 mmol) in THF (1.99 mL) was added to pieces of metallic magnesium (116 mg, 4.78 mmol) and the mixture was stirred at room temperature for 2 hours to prepare a Grignard reagent. To the reagent, a solution of zinc bromide (448 mg, 1.99 mmol) in THF (3.98 mL) was added and the mixture was stirred at room temperature for 30 minutes to prepare an organozinc reagent.

(2) In an argon atmosphere, a solution of nickel(II) chloride/DME complex (11 mg, 0.0501 mmol) and (R,R)-2,2'-isopropylidenebis(4-phenyl-2-oxazoline) (20 mg, 0.0598 mmol) in THF (5 mL) was prepared and 0.306 mL of the solution (0.0031 mmol of nickel(II) chloride/DME complex and 0.0037 mmol of (R,R)-2,2'-isopropylidenebis(4-phenyl-2-oxazoline; 0.1 mol % of nickel(II) chloride/DME complex and. 0.12 mol % of (R,R)-2,2'-isopropylidenebis(4-phenyl-2-oxazoline) relative to tert-butyl 2-bromopropanoate) was added to a solution of tert-butyl 2-bromopropanoate (640 mg, 3.06 mmol) in THF (3.92 mL) at 0° C. and the mixture was stirred at the same temperature for 5 minutes. Further, the entire amount of the organozinc reagent prepared in (1) above was added dropwise at 0° C. and the mixture was stirred at the same temperature for 20 hours. After adding a saturated aqueous solution of ammonium chloride, extraction was conducted with chloroform. The organic layer was separated with a phase separator and the solvent was distilled off under reduced pressure. Methanol was added to the residue and after stirring the mixture at room temperature for 30 minutes, the insoluble matter was filtered off and the filtrate was concentrated under reduced pressure. The resulting residue was purified by silica gel column chromatography (hexane/ethyl acetate=98:2 to 85:15) and the fractions containing the titled end compound were combined; the solvent was distilled off under reduced pressure to give the titled compound (770 mg) as a colorless solid.

The yield of the compound obtained is cited below.
Chemical yield: 84%
The $^1$H NMR and MS data for the compound obtained are given below.

$^1$H NMR (600 MHz, CHLOROFORM-d) δ ppm 1.43 (s, 9 H), 1.48 (d, J=7.0 Hz, 3 H), 3.64 (q, J=7.0 Hz, 1 H), 7.08-7.16 (m, 2 H), 7.33-7.40 (m, 2 H), 7.43 (t, J=7.6 Hz, 2 H), 7.54 (d, J=8.3 Hz, 2 H).
MS (ESI/APCI Dual pos.) m/z: 323 [M+Na]$^+$ The optical purity of the compound obtained and the conditions of HPLC analysis using a chiral column are cited below.
Column name: DAICEL CHIRALPAK OJ-3 (4.6 mmΦ× 250 mmL)
Eluting solution: hexane/ethanol=84:16
Flow rate: 1.0 mL/min
Column temperature: 40° C.
Retention time: R form=4.19 min; S form=4.60 min
Optical purity: 93% ee (S)

For its absolute configuration, the compound obtained was derived to 2-(2-fluorobiphenyl-4-yl)propanoic acid by the method of Example 9-6 to be described later and determination was made from the result of a specific rotation measurement conducted with reference to the data in Patent Literature, CN1356304 ([α]$^{20}_D$=+45.1 (c=1, EtOH)).

The 2-(2-fluorobiphenyl-4-yl)propanoic acid obtained was subjected to $^1$H NMR, MS and specific rotation measurements to give the following results.
$^1$H NMR (600 MHz, CHLOROFORM-d) δ ppm 1.52 (d, J=7.0 Hz, 3 H), 3.75 (q, J=7.0 Hz, 1 H), 7.08-7.16 (m, 2 H), 7.29-7.43 (m, 4 7.45-7.51 (m, 2 H).
MS (ESI/APCI Dual neg.) m/z: 243 [M−H]$^−$
[α]$^{20}_D$=+44.9±0.05 (c=1.01, EtOH)

The compound obtained was subjected to HPLC analysis using a chiral column under the following conditions.
Column name: DAICEL CHIRALPAK AY-H/SFC (4.6 mmΦ×250 mmL)
Eluting solution: methanol/carbon dioxide=10:90
Flow rate: 3.0 mL/min
Column temperature: 40° C.
Retention time: R form=2.37 min; S form=3.13 min
Optical purity: 97% ee (S)

Example 2-1

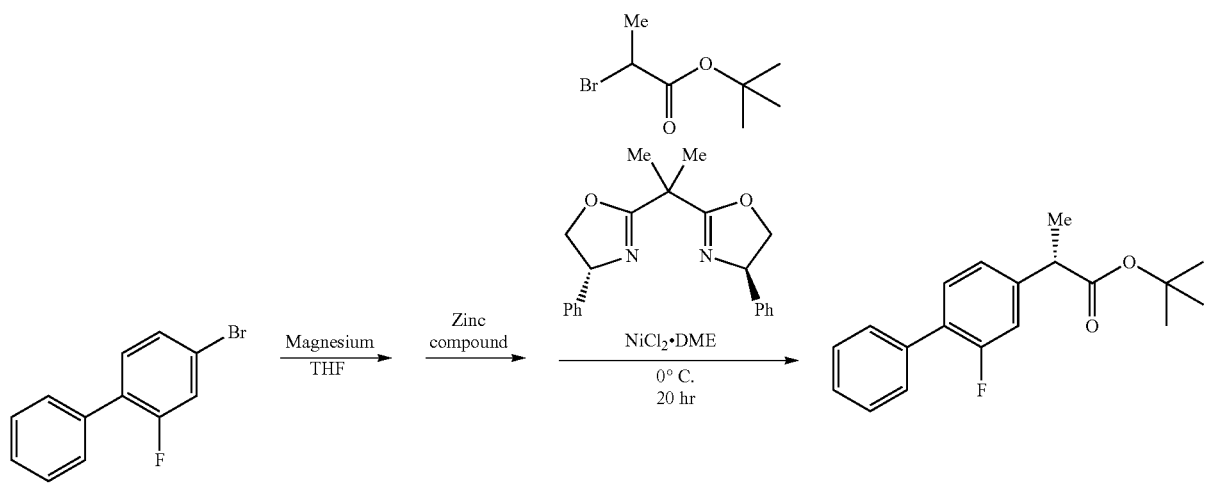

Using tert-butyl 2-bromopropanoate (640 mg, 3.06 mmol), nickel(II) chloride/DME complex (0.0031 mmol, 0.1 mol % relative to tert-butyl 2-bromopropanoate), and (R,R)-2,2'-isopropylidenebis(4-phenyl-2-oxazoline) (0.0037 mmol, 0.12 mol % relative to tert-butyl 2-bromopropanoate), reaction was carried out under the same conditions as in Example 1-1, with zinc bromide being changed to zinc chloride. The compounds used and the amounts of their use, as well as yield and optical purity data are shown in Table 1-1.

Example 2-2

Using tert-butyl 2-bromopropanoate (641 mg, 3.07 mmol), nickel(II) chloride/DME complex (0.031 mmol, 1.0 mol % relative to tert-butyl 2-bromopropanoate), and (R,R)-2,2'-isopropylidenebis(4-phenyl-2-oxazoline) (0.037 mmol, 1.2 mol % relative to tert-butyl 2-bromopropanoate), reaction was carried out under the same conditions as in Example 1-1 except that the pieces of metallic magnesium (116 mg, 4.78 mmol) were replaced by pieces of metallic magnesium (101 mg, 4.14 mmol), with the amount of zinc bromide being changed. The compounds used and the amounts of their use, yields and optical purities are shown in Table 1-1.

TABLE 1-1

| Ex. No. | Zn compound | Amount of Zn compound [mmol] | Amount of Grignard reagent [mmol] | Yield [%] | Optical purity [% ee]/ abs. config. |
|---|---|---|---|---|---|
| 2-1 | ZnCl | 1.99 | 3.98 | 76 | 92/(S) |
| 2-2 | ZnBr | 1.34 | 3.99 | 56 | 94/(S) |

Example 3-1 and Example 3-2

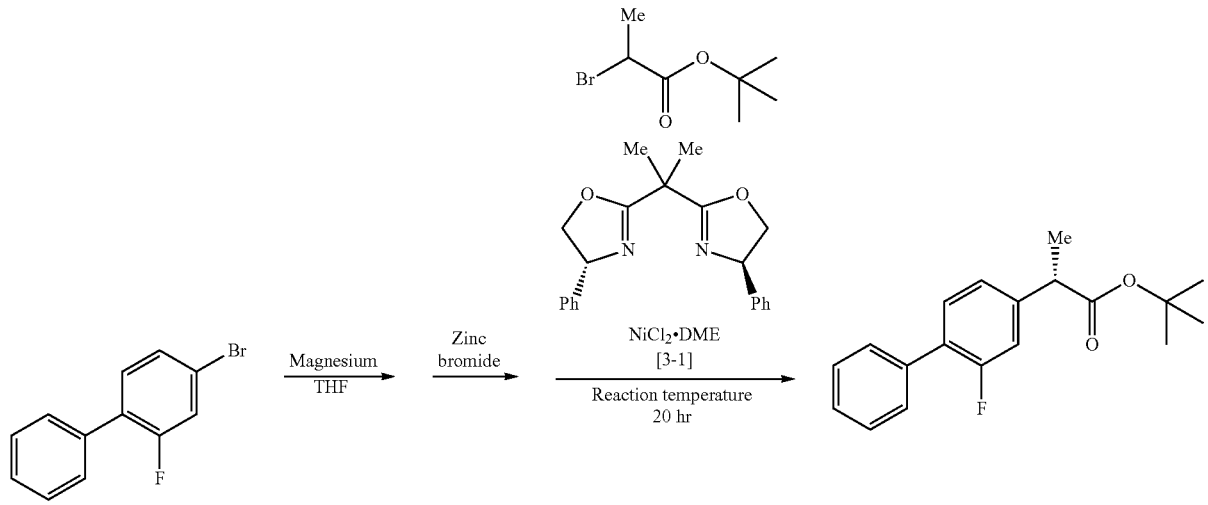

Using 4-bromo-2-fluorobiphenyl (1.007 g, 3.99 mmol), tert-butyl 2-bromopropanoate (641 mg, 3.07 mmol), and zinc bromide (1.99 mmol), reaction was carried out under the same conditions as in Example 1-1, with the reaction temperature being changed. The compounds used and the amounts of their use, yields, and optical purities are shown in Table 2-1.

Example 3-3 and Example 3-4

Using 4-bromo-2-fluorobiphenyl (1.007 g, 3.99 mmol), tert-butyl 2-bromopropanoate (641 mg, 3.07 mmol), and zinc bromide (1.99 mmol), reaction was carried out under the same conditions as in Example 1-1, with the amounts of use of nickel(II) chloride/DME complex and (R,R)-2,2'-isopropylidenebis(4-phenyl-2-oxazoline) (indicated as compound [3-1] in Table 2-1) being changed (each amount expressed in mol % relative to t-butyl 2-bromopropanoate). The compounds used and the amounts of their use, yields, and optical purities are shown in Table2-1.

TABLE 2-1

| Ex. No. | NiCl$_2$·DME [mol %] | Compound [3-1] [mol %] | Reaction temperature [° C.] | Yield [%] | Optical purity [% ee]/ abs. config. |
|---|---|---|---|---|---|
| 3-1 | 0.1 | 0.12 | 25 | 56 | 90/(S) |
| 3-2 | 0.1 | 0.12 | 15 | 65 | 93/(S) |
| 3-3 | 0.05 | 0.06 | 0 | 55 | 92/(S) |
| 3-4 | 0.03 | 0.036 | 0 | 54 | 91/(S) |

Example 4-1 to Example 4-10

Under the same conditions as in Example 1-1, reaction was carried out using different compounds than tert-butyl 2-bromopropanoate (0.1 mol % of nickel(II) chlorid/DME complex and 0.12 mol % of (R,R)-2,2'-isopropylidenebis(4-phenyl-2-oxazoline) relative to 2-bromopropanoate (indicated as compound [2-1] in Table 3-1)). The compounds used and the amounts of their use, yields, and optical purities are shown in Table 3-1.

TABLE 3-1

| Ex. No. | Structure of compound [2-1]: R$^1$ | Yield [%] | Optical purity [% ee]/ abs. config. |
|---|---|---|---|
| 4-1 | ⸺Et | 64 | 84/(S) |
| 4-2 | ⸺C(CH₃)₃ | 83 | 88/(S) |
| 4-3 | ⸺C(CH₃)₂Et | 53 | 96/(S) |
| 4-4 | ⸺CH₂CH=CH₂ | 61 | 86/(S) |
| 4-5 | ⸺cyclohexyl | 75 | 89/(S) |

[Formula 21]

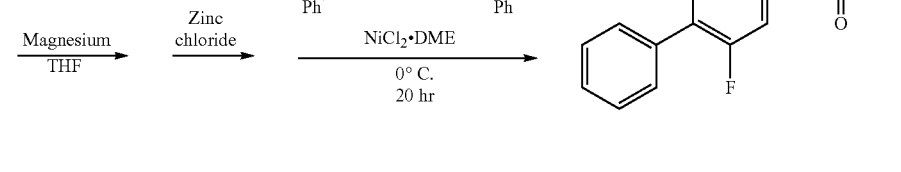

TABLE 3-1-continued

| Ex. No. | Structure of compound [2-1]: R¹ | Yield [%] | Optical purity [% ee]/ abs. config. |
|---|---|---|---|
| 4-6 | 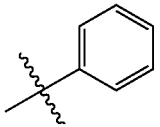 [SMILES: *c1ccccc1] | 61 | 84/(S) |
| 4-7 | 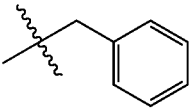 | 62 | 85/(S) |
| 4-8 | 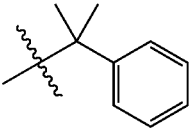 [SMILES: *C(C)(C)c1ccccc1] | 66 | 94/(S) |
| 4-9 | 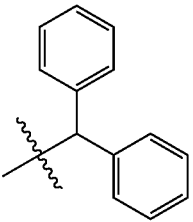 [SMILES: *C(c1ccccc1)c1ccccc1] | 69 | 88/(S) |
| 4-10 | 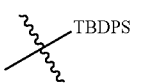 TBDPS | 79 | 91/(S) |

The $^1$H NMR and MS data for the compound obtained in Example 4-1 are cited below. $^1$H NMR (600 MHz, CHLOROFORM-d) δ ppm 1.25 (t, J=7.2 Hz, 3 H), 1.53 (d, J=7.2 Hz, 3 H), 3.74 (q, J=7.2 Hz, 1 H), 4.11-4.24 (m, 2 H), 7.09-7.18 (m, 2 H), 7.35-7.47 (m, 4 H), 7.50-7.57 (m, 2 H).

MS (ESI/APCI Dual pos.) m/z: 273 [M+H]$^+$

The compound obtained in Example 4-1 was subjected to HPLC analysis under the following conditions using a chiral column.
Column name: DAICEL CHIRALPAK OJ-3 (4.6 mmΦ× 250 mmL)
Eluting solution: hexane/ethanol=84:16
Flow rate: 1.0 mL/min
Column temperature: 40° C.
Retention time: R form=150 min; S form 6.18 min The $^1$H NMR and MS data for the compound obtained in Example 4-2 are cited below.
$^1$H NMR (600 MHz, CHLOROFORM-d) δ ppm 0.88 (s, 9 H), 1.56 (d, J=7.4 Hz, 3 H), 3.73-3.85 (m, 3 H), 7.10-7.19 (m, 2 H), 7.34-7.47 (m, 4 H), 7.49-7.58 (m, 2 H).

MS (ESI/APCI Dual pos.) m/z: 337 [M+Na]$^+$

The compound obtained in Example 4-2 was subjected to HPLC analysis under the following conditions using a chiral column.
Column name: DAICEL CHIRALPAK AD-3×2 (4.6 mmΦ× 150 mmL×2)
Eluting solution: hexane:ethanol=96:4
Flow rate: 1.0 mL/min
Column temperature: 40° C.
Retention time: R form=4.44 min; S form=5.54 min The $^1$H NMR and MS data for the compound obtained in Example 4-3 are cited below.

$^1$H NMR (600 MHz, CHLOROFORM-d) δ ppm 0.80 (t, J=7.6 Hz, 3 H), 1.36-1.43 (m, 6 H), 1.49 (d, J=7.2 Hz, 3 H), 1.70-1.83 (m, 2 H), 3.66 (q, J=7.2 Hz, 1 H), 7.09-7.17 (m, 2 H), 7.34-7.47 (m, 4 H), 7.49-7.59 (m, 2 H).

MS (ESI/APCI Dual pos.) m/z: 315 [M+H]$^+$

The compound obtained in Example 4-3 was subjected to HPLC analysis under the following conditions using a chiral column.
Column name: DAICEL CHIRALPAK OJ-3 (4.6 mmΦ× 250 mmL)
Eluting solution: hexane:ethanol=84:16
Flow rate: 1.0 mL/min
Column temperature: 40° C.
Retention time: R form=4.02 min; S form=4.31 min The $^1$H NMR and MS data for the compound obtained in Example 4-4 are cited below.
$^1$H NMR (600 MHz, CHLOROFORM-d) δ ppm 1.55 (d, J=7.2 Hz, 3 H), 3.79 (q, J=7.2 Hz, 1 H), 4.55-4.68 (m, 2 H), 5.19-5.30 (m, 2 H), 5.82-5.95 (m, 1 H), 7.11-7.19 (m, 2 H), 7.34-7.47 (m, 4 H), 7.50-7.57 (m, 2 H).

MS (ESI/APCI Dual pos,) m/z: 285 [M+H]$^+$

The compound obtained in Example 4-4 was subjected to HPLC analysis under the following conditions using a chiral column.
Column name: DAICEL CHIRALPAK OJ-3 (4.6 mmΦ× 250 mmL)
Eluting solution: hexane:ethanol=84:16
Flow rate: 1.0 mL/min
Column temperature: 40° C.
Retention time: R form=6.18 min; S form=6.91 min The $^1$H NMR and MS data for the compound obtained in Example 4-5 are cited below.
$^1$H NMR (600 MHz, CHLOROFORM-d) δ ppm 1.14-1.90 (m, 10 H), 1.50-1.55 (m, 3 H), 3.72 (q, J=7.3 Hz, 1 H), 4.74-4.87 (m, 1 H), 7.10-7.18 (m, 2 H), 7.27-7.47 (m, 4 H), 7.49-7.59 (m, 2 H).

MS (ESI/APCI Dual pos.) m/z: 327 [M+H]$^+$

The compound obtained in Example 4-5 was subjected to HPLC analysis under the following conditions using a chiral column.
Column name: DAICEL CHIRALPAK OJ-3 (4.6 mmΦ× 250 mmL)
Eluting solution: hexane:ethanol=84:16
Flow rate: 1.0 mL/min
Column temperature: 40° C.
Retention time: R form=4.61 min; S form=5.15 min The $^1$H NMR and MS data for the compound obtained in Example 4-6 are cited below.
$^1$H NMR (600 MHz, CHLOROFORM-d) δ ppm 1.66 (d, J=7.0 Hz, 3 H), 4.00 (q, J=7.0 Hz, 1 H), 7.01-7.06 (m, 2 H), 7.19-7.28 (m, 3 H), 7.33-7.48 (m, 6 H), 7.54-7.58 (m, 2 H).

MS (ESI/APCI Dual pos.) m/z: 343 [M+Na]$^+$

The compound obtained in Example 4-6 was subjected to HPLC analysis under the following conditions using a chiral column.
Column name: DAICEL CHIRALPAK OJ-3 (4.6 mmΦ× 250 mmL)
Eluting solution: hexane:ethanol=84:16
Flow rate: 1.0 mL/min
Column temperature: 40° C.
Retention time: R form=22.7 min; S form=26.9 min.

The $^1$H NMR and MS data for the compound obtained in Example 4-7 are cited below.
$^1$H NMR (600 MHz, CHLOROFORM-d) δ ppm 1.54-1.57 (m, 3 H), 3.81 (q, J=7.3 Hz, 1H), 5.05-5.21 (m, 2 H), 7.09-7.16 (m, 2 H), 7.26-7.39 (m, 7 H), 7.42-7.47 (m, 2 H), 7.51-7.56 (m, 2 H).

MS (ESI/APCI Dual pos.) m/z: 357 [M+Na]+

The compound obtained in Example 4-7 was subjected to HPLC analysis under the following conditions using a chiral column.

Column name: DAICEL CHIRALPAK OJ-3 (4.6 mmΦ× 250 mmL)
Eluting solution: hexane:ethanol=84:16
Flow rate: 1.0 mL/min
Column temperature: 40° C.
Retention time: S form=10.5 min; R form=12.4 min The $^1$H NMR and MS data for the compound obtained in Example 4-8 are cited below.

$^1$H NMR (600 MHz, CHLOROFORM-d) δ ppm 1.49 (d, J=7.2 Hz, 3 H), 1.71 (s, 3H), 1.77 (s, 3H), 3.73 (q, J=7.2 Hz, 1 H), 7.06-7.15 (m, 2 H), 7.16-7.29 (m, 5 H), 7.32-7.49 (m, 4H), 7.53-7.60 (m, 2 H).

MS (ESI/APCI Dual pos.) m/z: 385 [M+Na]+

The compound obtained in Example 4-8 was subjected to HPLC analysis under the following conditions using a chiral column.

Column name: DAICEL CHIRALPAK OJ-3 (4.6 mmΦ× 250 mmL)
Eluting solution: hexane:ethanol=84:16
Flow rate: 1.0 mL/min
Column temperature: 40° C.
Retention time: S form=8.23 min; R form=9.19 min The $^1$H NMR and MS data for the compound obtained in Example 4-9 are cited below.

$^1$H NMR (600 MHz, CHLOROFORM-d) δ ppm 1.56 (d, J=7.2 Hz, 3 H), 3.87 (q, J=7.2 Hz, 1 H), 6.85 (s, 1 H), 7.06-7.17 (m, 4 H), 7.20-7.40 (m, 10 H), 7.42-7.48 (m, 2 H), 7.51-7.57 (m, 2 H).

MS (ESI/APCI Dual pos.) m/z: 433 [M+Na]+

The compound obtained in Example 4-9 was subjected to HPLC analysis under the following conditions using a chiral column.

Column name: DAICEL CHIRALPAK OJ-3 (4.6 mmΦ× 250 mmL)
Eluting solution: hexane:ethanol=84:16
Flow rate: 1.0 mL/min
Column temperature: 40° C.
Retention time: S form=16.2 min; R form=17.7 min The $^1$H NMR and MS data for the compound obtained in Example 4-10 are cited below.

$^1$H NMR (600 MHz, CHLOROFORM-d) δ ppm 1.01 (s, 9 H), 1.58 (d, J=7.2 Hz, 3 H), 3.88 (q, J=7.2 Hz, 1 H), 7.12-7.21 (m, 2 H), 7.29-7.73 (m, 16 H).

MS (ESI/APCI Dual pos.) m/z: 505 [M+Na]+

Concerning their absolute configurations, the compounds obtained were each derived to 2-(2-fluorobiphenyl-4-yl)propanoic acid by the method of Example 9-6 described later for the products of Examples 4-1 to 4-6 and by the methods described below for the products of Examples 4-7 to 4-10; the derivative was then subjected to HPLC analysis using the chiral column described in Example 1-1, as a result of which the derivatives was each determined to be an S form.

The compound (100 mg) obtained in Example 4-7 was dissolved in methanol (3 mL) and after adding 10% palladium/activated carbon (20 mg), the reaction solution was stirred at room temperature for 3 hours under a hydrogen atmosphere. The reaction solution was filtered through Celite (registered trademark) to remove the insoluble matter and, thereafter, the filtrate was concentrated under reduced pressure. The resulting residue was purified by silica gel column chromamtography (hexane:ethyl acetate=90:10 to 85:15) and the fractions containing the titled end compound were collected; the solvent was distilled off under reduced pressure to give 2-(2-fluorobiphenyl-4-yl)propanoic acid (66 mg) as a colorless solid.

The optical purity of the obtained compound was measured by HPLC analysis using a chiral column in accordance with the same method as in Example 1-1.

Optical purity: 84% ee (S)

The compound (50 mg) obtained in Example 4-8 was dissolved in chloroform (0.3 mL) and after adding TFA (0.106 mL), the reaction solution was stirred at room temperature for 3 hours. Water was added to the reaction solution which was then extracted with chloroform twice. The organic layer was separated with a phase separator and the solvent was distilled off under reduced pressure. The resulting residue was purified by silica gel column chromamtography (hexane:ethyl acetate=88:12 to 10:90) and the fractions containing the titled end compound were collected; the solvent was distilled off under reduced pressure to give 2-(2-fluorobiphenyl-4-yl)propanoic acid (29 mg) as a colorless solid.

The optical purity of the obtained compound was measured by HPLC analysis using a chiral column in accordance with the same method as in Example 1-1.

Optical purity: 95% ee (S)

The compound (57 mg) obtained in Example 4-9 was dissolved in chloroform (0.3 mL) and after adding TFA (0.106 mL), the reaction solution was stirred at room temperature for 3 hours, then at 60° C. for 3 hours. Water was added to the reaction solution which was then extracted with chloroform twice. The organic layer was separated with a phase separator and the solvent was distilled off under reduced pressure. The resulting residue was purified by silica gel column chromamtography (hexane:ethyl acetate=88:12 to 10:90) and the fractions containing the titled end compound were collected; the solvent was distilled off under reduced pressure to give 2-(2-fluorobiphenyl-4-yl)propanoic acid (34 mg) as a colorless solid.

The optical purity of the obtained compound was measured by HPLC analysis using a chiral column in accordance with the same method as in Example 1-1.

Optical purity: 89% ee (S)

The compound (30 mg) obtained in Example 4-10 was dissolved in tetrahydrofuran and after adding a tetra-n-butylammonium fluoride/1 M tetrahydrofuran solution (0.124 mL), the mixture was stirred at room temperature for 8 hours. To the reaction solution, water and 1 M hydrochloric acid were added for pH adjustment to between 3 and 4, followed by two extractions with chloroform. After separating the organic layer with a phase separator, the solvent was distilled off under reduced pressure to give 2-(2-fluorobiphenyl-4-yl)propanoic acid (30 mg) as a colorless solid.

The optical purity of the obtained compound was measured by HPLC analysis using a chiral column in accordance with the same method as in Example 1-1.

Optical purity: 91% ee (S)

Example 5-1 to Example 5-4

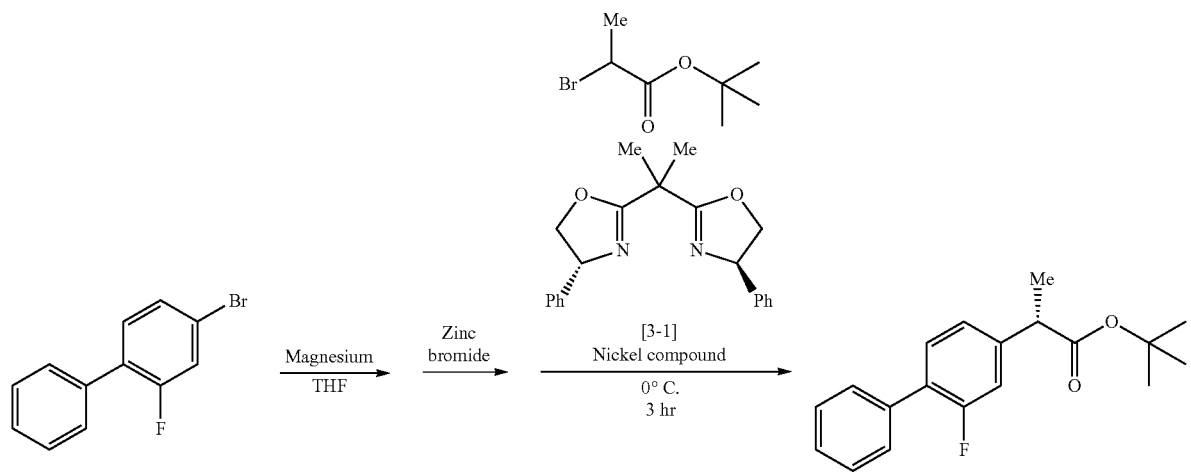

[Formula 22]

Under the same conditions as in. Example 1-1, reaction was carried out using a THF solution of an organozinc reagent in an amount of 6.0 mL (1.36 mmol, 0.90 equivalents relative to t-butyl 2-bromopropanoate) and (R,R)-2,2'-isopropylidenebis(4-phenyl-2-oxazoline) (cited as compound [3-1] in Table 4-1 and the amount of its use also cited in Table 4-1 in terms of mol % relative to t-butyl 2-bromopropanoate), with the nickel(II) chloride/DME complex being changed to different compounds which were used in different amounts (cited in terms of mol % relative to t-butyl 2-bromopropanoate). The compounds used and their amounts, as well as yield and optical purity data are shown in Table 4-1.

In the Examples under consideration, the nickel(II) chloride/DME complex and compound [3-2] were used in the same manner as in Example 1-1: THF solutions of these compounds were preliminarily made and the amounts required for reaction were metered for subsequent use.

TABLE 4-1

| Ex. No. | Nickel compound | Amount of nickel compound [mol %] | Compound [3-1] [mol %] | Yield [%] | Optical purity [% ee]/ abs. config. |
|---|---|---|---|---|---|
| 5-1 | $NiCl_2$ | 0.31 | 0.38 | 65 | 92/(S) |
| 5-2 | $NiCl_2(PPh_3)_2$ | 0.10 | 0.12 | 67 | 94/(S) |
| 5-3 | $NiI_2$ | 0.30 | 0.38 | 68 | 93/(S) |
| 5-4 | $Ni(acac)_2$ | 0.10 | 0.12 | 65 | 93/(S) |

Example 6-1 to Example 6-2

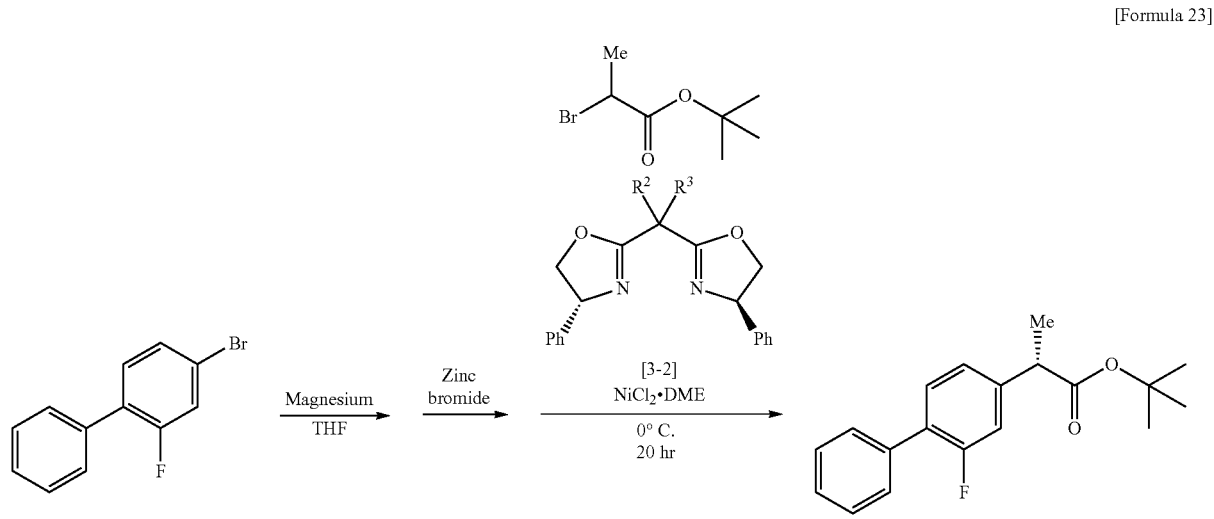

[Formula 23]

Under the same conditions as in Example 1-1, reaction was carried out using 4-bromo-2-fluorobiphenyl (999 mg, 3.98 mmol), tert-butyl 2-bromopropanoate (640 mg, 3.06 mmol), zinc bromide (2.9 mmol), and a nickel(II) chloride/DME complex (0.0031 mmol, 0.1 mol % relative to t-butyl 2-bromopropanoate), with (R,R)-2,2'-isopropylidenebis(4-phenyl-2-oxazoline) being changed to different compounds. The compounds used (cited as compound [3-2] in Table 5-1) and the amounts of their use (cited in terms of mol % relative to t-butyl 2-bromopropanoate) as well as yield and optical purity data are shown in Table 5-1.

In the Examples under consideration, the nickel(II) chloride/DME complex and compound [3-2] were used in the same manner as in Example 1-1: THF solutions of these compounds were preliminarily made and the amounts required for reaction were metered for subsequent use.

TABLE 5-1

| Ex. No. | Structure of compound [3-2]: 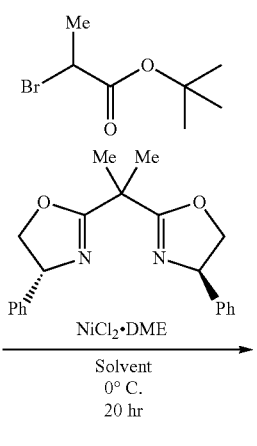 | Amount of compound [3-2] in equivalents [mol %] | Yield [%] | Optical purity [% ee]/ abs. config. |
|---|---|---|---|---|
| 6-1 | (R²=Me, R³=Me) | 0.12 | 48 | 91/(S) |
| 6-2 | (Et, Et) | 0.12 | 64 | 88/(S) |
| | (cyclopropyl) | | | |

Example 7-1 to Example 7-5

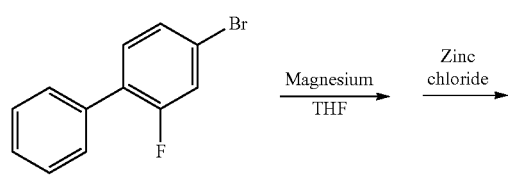

[Formula 24]

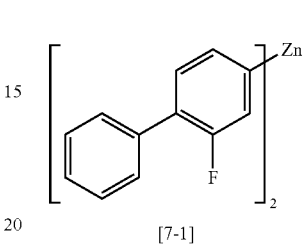

[7-1]

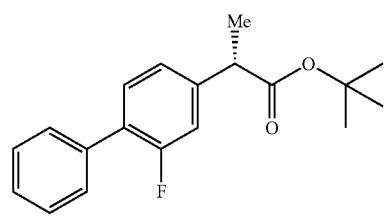

Under the same conditions as in Example 1-1, reaction was carried out changing the amount of tert-butyl 2-bromopropanoate to 209 mg (1.0 mmol) and using a THF solution of an organozinc reagent (compound [7-1]) in an amount of 1.5 ml (0.341 mmol, 0.68 equivalents of tert-butyl 2-bromopropanoate), a nickel(II) chloride/DME complex (0.0010 mmol, 0.1 mol % relative to tert-butyl 2-bromopropanoate), and (R,R)-2,2'-isopropylidenebis(4-phenyl-2-oxazoline) (0.0012 mmol, 0.12 mol % relative to tert-butyl 2-bromopropanoate), with the solvent being changed to different types. The solvents used, yields and optical purities are shown in Table 6-1.

As previously mentioned, compound [7-1] was prepared using 0.5 equivalents of zinc chloride relative to the prepared organomagnesium reagent.

TABLE 6-1

| Ex. No. | Solvent | Yield [%] | Optical purity [% ee]/ abs. config. |
|---|---|---|---|
| 7-1 | THF | 62 | 92/(S) |
| 7-2 | 1,4-dioxane | 55 | 93/(S) |
| 7-3 | 2-MeTHF | 58 | 93/(S) |
| 7-4 | toluene | 61 | 93/(S) |
| 7-5 | ethyl acetate | 60 | 92/(S) |

Example 8-1

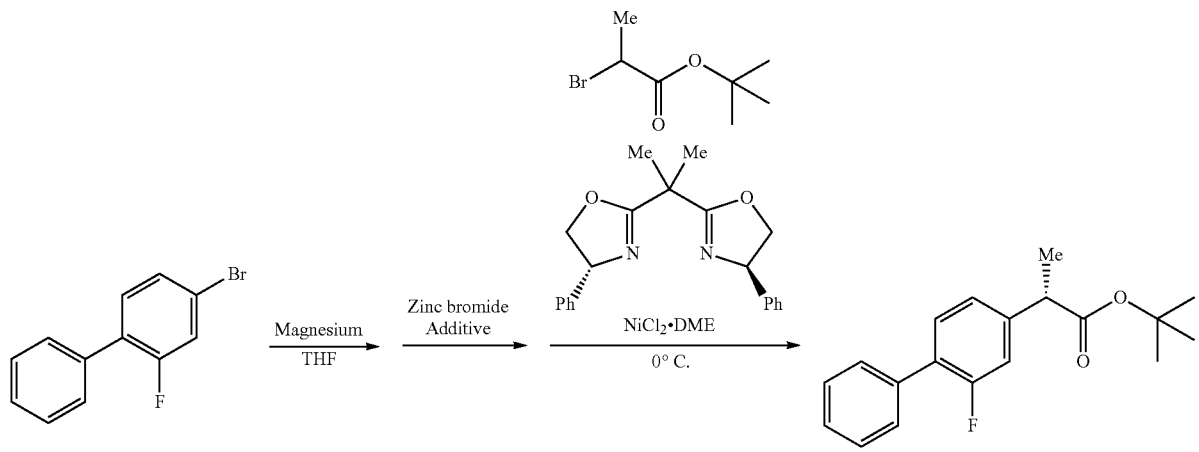

[Formula 25]

In the above scheme, "Additive" is ethyl acetate or lithium bromide.

Under the same conditions as in Example 1-1, an organozine reagent was prepared and, thereafter, ethyl acetate (20 times the amount of 4-bromo-2-fluorobiphenyl) was added to make a solvent mixture with THF and a coupling reaction with tert-butyl 2-bromopropanoate was carried out for 3 hours. Purification was performed not by silica gel column chromatography but by recrystallization using an ethanol-water (3:1) mixed solvent.

The yield of the compound obtained is cited below.
Chemical yield: 75%
The optical purity of the compound obtained is cited below.
Optical purity: 99% ee (S)

Example 8-2

Under the same conditions as in Example 1-1, an organozinc reagent was prepared and, thereafter, lithium bromide (1 equivalent relative to tert-butyl 2-bromopropanoate) was added and a coupling reaction with tert-butyl 2-bromopropanoate was carried out for 2 hours.

The yield of the compound obtained is cited below.
Chemical yield: 55%
The optical purity of the compound obtained is cited below.
Optical purity: 89% ee (S)

Example 9-1

Method of producing (S)-2-(2-fluorobiphenyl-4-yl)propanoic acid

[Formula 26]

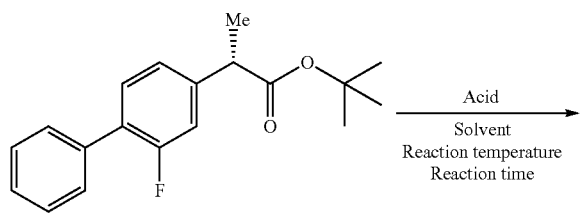

-continued

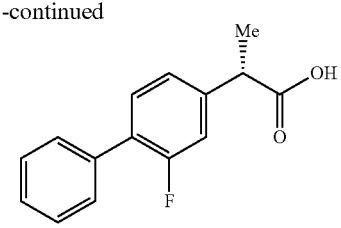

To tert-butyl (S)-2-(2-fluorobiphenyl-4-yl)propanoate (37.0 g, 123 mmol), heptane (111 mL) and formic acid (111 mL) were added and the mixture was stirred at room temperature for 20 hours. After adding toluene (74 mL) and water (111 mL), the mixture was stirred for an hour at an internal temperature of 50° C. The organic layer was separated and washed with water (111 mL, 50° C.). Heptane (333 mL) was added to the organic layer which was dissolved by heating to an internal temperature of 70° C. After leaving the solution to cool under stirring, a seed obtained by the method set out below was added at 60° C., followed by stirring at room temperature for an hour, then under ice cooling for an hour. The solid crystallizing out was recovered by filtration and washed with heptane (148 mL, 5° C.). The resulting solid was dried under reduced pressure to give the titled compound (25.5 g) as a colorless powder. Its yield and optical purity are shown in Table 7-1.

The $^1$H NMR and MS data for the compound obtained are given below.

$^1$H NMR (600 MHz, CHLOROFORM-d) δ ppm 1.52 (d, J=7.0 Hz, 3 H), 3.75 (q, J=7.0 Hz, 1H), 7.08-7.16 (m, 2 H), 7.29-7.43 (m, 4 H), 7.45-7.51 (m, 2 H).

MS (ESI/APCI Dual neg.) m/z: 243 [M−H]⁻

The compound obtained was subjected to HPLC analysis using a chiral column under the following conditions.
Column name: DAICEL CHIRALPAK AY-H/SFC (4.6 mmΦ×250 mmL)
Eluting solution:methanol/carbon dioxide=10:90
Flow rate: 3.0 mL/min
Column temperature: 40° C.

The seed crystal used in Example 9-1 was obtained by the following method.

Using tert-butyl (S)-2-(2-fluorobiphenyl-4-yl)propanoate (4.88 g. 16.2 mmol), reaction and post-treatment were carried out by the same method as in Example 9-1, and the organic layer obtained was concentrated under reduced pressure. The resulting residue was dissolved in toluene (4.9 mL) and heptane (49 mL) at an internal temperature of 90° C. and the solution was left to cool under stirring, followed by stirring at room temperature for an hour, then under ice cooling for an hour. The crystallizing solid was recovered by filtration and washed with heptane (19.5 mL, 5° C.). The resulting solid was dried under reduced pressure to give (S)-2-(2-fluorobiphenyl-4-yl)propanoic acid (3.51 g, optical purity: 99% ee (S)) as a colorless powder. One gram of the powder obtained was dissolved in toluene (2 mL) and heptane (12 mL) at an internal temperature of 70° C. and the solution was left to cool under stirring, followed by stirring at room temperature for an hour, then under ice cooling for an hour. The crystallizing solid was recovered by filtration and washed with heptane (4 mL, 5° C.). The resulting solid was dried under reduced pressure to give (S)-2-(2-fluorobiphenyl-4-yl)propanoic acid (950 mg) as a colorless powder for use as a seed crystal.

Example 9-2 to Example 9-9

Reaction was carried out under the same conditions as in. Example 9-1, except for the reaction temperature, reaction time, as well as the acids and solvents to be used. The compounds used, yields and optical purities are shown in Table 7-1.

TABLE 7-1

| Ex. No. | Acid | Solvent | Reaction temperature [° C.] | Time [hr] | Yield [%] | Optical purity [% ee]/abs. config. |
|---|---|---|---|---|---|---|
| 9-1 | Formic acid | Heptane | rt | 20 | 85 | >99/(S) |
| 9-2 | Formic acid | None | rt | 20 | 90 | >99/(S) |
| 9-3 | Trifluoroacetic acid | Toluene | rt | 20 | 91 | 99/(S) |
| 9-4 | Hydrochloric acid | 1,4-dioxane | rt | 40 | 78 | 99/(S) |
| 9-5 | Conc. hydrochloric acid | Acetic acid | rt | 40 | 84 | 99/(S) |
| 9-6 | 10% sulfuric acid aq. sol. | Acetic acid | 80 | 2 | 89 | 99/(S) |
| 9-7 | Tosylic acid monohydrate | Toluene | 80 | 2 | 93 | 99/(S) |
| 9-8 | Mesylic acid | Toluene | rt | 1 | 90 | 99/(S) |
| 9-9 | 88% formic acid aq. sol. | Toluene | 80 | 5 | 92 | 99/(S) |

Example 10-1

Under the same conditions as in Example 1-1(1) but without adding zinc bromide, a Grignard reagent was prepared instead of the organozinc reagent. Using the prepared Grignard reagent (47.8 mmol), tert-butyl 2-bromopropanoate (10 g, 47.8 mmol), a nickel(II) chloride/DME complex (0.478 mmol, 1 mol % relative to tert-butyl 2-bromopropanoate), and (R,R)-2,2'-isopropylidenebis(4-phenyl-2-oxazoline) (0.574 mmol, 1.2 mol % relative to tert-butyl 2-bromopropanoate), a coupling reaction was carried out under the same conditions as in Example 1-1(2) at a reaction temperature of −20° C. for a reaction time of 24 hr.

The yield of the obtained compound is cited below.
Chemical yield: 72%
The optical purity of the obtained compound is cited below.
Optical purity: 86% ee (S)

Example 10-2

Under the same conditions as in Example 1-1(1) but without adding zinc bromide, a Grignard reagent was prepared instead of the organozinc reagent. Using the prepared Grignard reagent (12 mmol), tert-butyl 2-bromopropanoate (2.09 g, 10 mmol), a nickel(II) chloride/DME complex (0.1 mmol, 1 mol % relative to tert-butyl 2-bromopropanoate), and (R,R)-2,2'-isopropylidenebis(4-phenyl-2-oxazoline) (0.12 mmol, 1.2 mol % relative to tert-butyl 2-bromopropanoate), a coupling reaction was carried out under the same conditions as in Example 1-1(2) at a reaction temperature of −20° C. for a reaction time of 24 hr.

The yield of the obtained compound is cited below.
Chemical yield: 89%
The optical purity of the obtained compound is cited below.
Optical purity: 87% ee (S)

Example 10-3

Under the same conditions as in Example 1-1(1) but without adding zinc bromide, a Grignard reagent was prepared instead of the organozinc reagent. Using the prepared Grignard reagent (10 mmol), tert-butyl 2-bromopropanoate (2.09 g, 10 mmol), a nickel(II) chloride/DME complex (0.05 mmol, 0.5 mol % relative to tert-butyl 2-bromopropanoate), and (R,R)-2,2'-isopropylidenebis(4-phenyl-2-oxazoline) (0.06 mmol, 0.6 mol % relative to tert-butyl 2-bromopropanoate), a coupling reaction was carried out under the same conditions as in Example 1-1(2) at a reaction temperature of −10° C. for a reaction time of 3 hr.

The yield of the obtained compound is cited below.
Chemical yield: 72%
The optical purity of the obtained compound is cited below.
Optical purity: 87% ee (S)

Example 10-4

Under the same conditions as in Example 1-1(1) but without adding zinc bromide, a Grignard reagent was prepared instead of the organozinc reagent. Using the prepared Grignard reagent (10 mmol), tert-butyl 2-bromopropanoate (2.09 g, 10 mmol), a nickel(II) chloride/DME complex (0.1 mmol, 1 mol % relative to tert-butyl 2-bromopropanoate), and (R,R)-2,2'-isopropylidenebis(4-phenyl-2-oxazoline) (0.12 mmol, 1.2 mol % relative to tert-butyl 2-bromopropanoate), a coupling reaction was carried out under the same conditions as in Example 1-1(2) at a reaction temperature of −10° C. for a reaction time of 3 hr.

The yield of the obtained compound is cited below.
Chemical yield: 73%
The optical purity of the obtained compound is cited below.
Optical purity: 89% ee (S)

Example 10-5

Under the same conditions as in Example 1-1(1) but without adding zinc bromide, a Grignard reagent was prepared instead of the organozinc reagent. Using the prepared Grignard reagent (10 mmol), tert-butyl 2-bromopropanoate (2.09 g, 10 mmol), a nickel(II) chloride/DME complex (0.1 mmol, 1 mol % relative to tert-butyl 2-bromopropanoate), and (R,R)-2,2'-isopropylidenebis(4-phenyl-2-oxazoline) (0.12 mmol, 1.2 mol % relative to tert-butyl 2-bromopropanoate), a coupling reaction was carried out under the same conditions as in Example 1-1(2) for a reaction time of 3 hr.

The yield of the obtained compound is cited below.
Chemical yield: 72%
The optical purity of the obtained compound is cited below.
Optical purity: 86% ee (S)

Example 10-6

Under the same conditions as in Example 1-1(1) but without adding zinc bromide, a Grignard reagent was prepared instead of the organozinc reagent. Using the prepared Grignard reagent (10 mmol), a nickel(II) chloride/DME complex (0.1 mmol, 1 mol % relative to tert-butyl 2-chloropropanoate), and (R,R)-2,2'-isopropylidenebis(4-phenyl-2-oxazoline) (0.12 mmol, 1.2 mol % relative to tert-butyl 2-chloropropanoate), a coupling reaction was carried out under the same conditions as in Example 1-1(2) for a reaction time of 24 hr, except that tert-butyl 2-bromopropanoate was replaced by tert-butyl 2-chloropropanoate (1.65 g, 10 mmol).
Chemical yield: 60%
The optical purity of the obtained compound is cited below.
Optical purity: 94% ee (S)

Example 10-7

Under the same conditions as in Example 1-1(1) but without adding zinc bromide, a Grignard reagent was prepared instead of the organozinc reagent. Using the prepared Grignard reagent (10 mmol), a nickel(II) chloride/DME complex (0.1 mmol, 1 mol % relative to tert-butyl 2-chloropropanoate), and (R,R)-2,2'-isopropylidenebis(4-phenyl-2-oxazoline) (0.12 mmol, 1.2 mol % relative to tert-butyl 2-chloropropanoate), a coupling reaction was carried out under the same conditions as in Example 1-1(2) for a reaction time of 24 hr, except that tert-butyl 2-bromopropanoate was replaced by ethyl 2-chloropropanoate (1.37 g, 10 mmol).

The yield of the obtained compound is cited below.
Chemical yield: 79%
The optical purity of the obtained compound is cited below.
Optical purity: 85% ee (S)

Example 10-8

Under the same conditions as in Example 1-1(1) but without adding zinc bromide, a Grignard reagent was prepared instead of the organozinc reagent. Using the prepared Grignard reagent (2.0 mmol), tert-butyl 2-bromopropanoate (0.42 g, 2.0 mmol), and a nickel(II) chloride/DME complex (0.1 mmol, 5 mol % relative to tert-butyl 2-bromopropanoate), a coupling reaction with tert-butyl 2-bromopropanoate was carried out under the same conditions as in Example 1-1(2) at a reaction temperature of −20° C. for a reaction time of 3 hr, except that (R,R)-2,2'-isopropylidenebis(4-phenyl-2-oxazoline) was replaced by (R,R)-2,2'-(pentane-3,3-diyl)bis(4-phenyl-2-oxazoline) (0.12 mmol, 6 mol % relative to test-butyl 2-bromopropanoate).

The yield of the obtained compound is cited below.
Chemical yield: 53%
The optical purity of the obtained compound is cited below.
Optical purity: 90% ee (S)

INDUSTRIAL APPLICABILITY

According to the present invention, optically active 2-(2-fluorobiphenyl-4-yl)propanoic acid which is useful as a pharmaceutical can be produced with high optical purity.

The invention claimed is:

1. A process for producing a compound of formula [4]

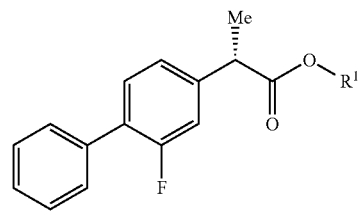

comprising:

(a) preparing an organometallic reagent by reacting a compound of formula [1]

with magnesium; and (b) reacting a compound of formula [2]

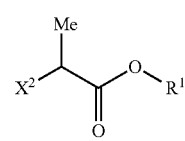

with the organometallic reagent prepared in (a) in the presence of a catalytic amount of a nickel compound and a catalytic amount of an optically active compound of formula [3]

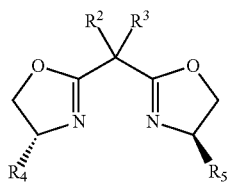

to obtain the compound of formula [4];
wherein
X¹ represents a halogen atom;
X² represents a halogen atom;
R¹ represents tert-butyldiphenylsilyl, $C_{1-6}$ alkyl, $C_{2-6}$ alkenyl, $C_{3-8}$ cycloalkyl, phenyl, or benzyl optionally substituted with one or two groups selected from group A1 of substituents;
R² and R³ independently represent $C_{1-6}$ alkyl, or R², R³ and the carbon atom adjacent to said substituents may, taken together, form $C_{3-6}$ cycloalkane;
R⁴ and R⁵ independently represent $C_{1-6}$ alkyl, benzyl, phenethyl, or phenyl optionally substituted with one or two groups selected from group A2 of substituents, wherein
group A1 of substituents consists of $C_{1-6}$ alkyl and phenyl, and
group A2 of substituents consists of a halogen atom, $C_{1-6}$ alkyl, halo-$C_{3-6}$ alkyl, $C_{1-6}$ alkoxy, halo-$C_{1-6}$ alkoxy, and phenyl.

2. The process according to claim 1, wherein the compound of formula [1], after being reacted with magnesium in (a), is further reacted with zinc chloride or zinc bromide to prepare the organometallic reagent.

3. The process according to claim 1, further comprising:
(c) converting the obtained compound of formula [4] to a compound of formula [5]

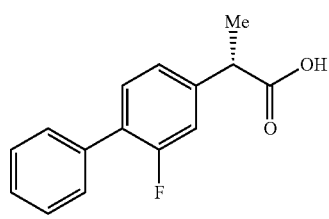

or a pharmaceutically acceptable salt thereof.

4. The process according to claim 3, wherein the compound of formula [1], after being reacted with magnesium in (a), is further reacted with zinc chloride or zinc bromide to prepare the organometallic reagent.

5. The process according to claim 1, wherein R¹ of the compound of formula [2] in (b) is $C_{1-6}$ alkyl.

6. The process according to claim 1, wherein R¹ of the compound of formula [2] in (b) is tert-butyl.

7. The process according to claim 1, wherein, relative to the compound of formula [2], the catalytic amount of the nickel compound used in (b) is no more than 10 mol %.

8. The process according to claim 1, wherein, relative to the compound of formula [2], the catalytic amount of the optically active compound of formula [3] used in (b) is no more than 12 mol %.

9. The process according to claim 2, wherein, relative to the compound of formula [2], the catalytic amount of the nickel compound used in (b) is from 0.03 to 1.00 mol % and the catalytic amount of the optically active compound of formula [3] used in (b) is from 0.036 to 1.20 mol %.

10. The process according to claim 4, wherein, relative to the compound of formula [2], the catalytic amount of the nickel compound used in (b) is from 0.03 to 1.00 mol % and the catalytic amount of the optically active compound of formula [3] used in (b) is from 0.036 to 1.20 mol %.

11. The process according to claim 1, wherein, relative to the compound of formula [2], the catalytic amount of the nickel compound used in (b) is from 0.50 to 1.00 mol % and the catalytic amount of the optically active compound of formula [3] used in (b) is from 0.60 to 1.20 mol %.

12. The process according to claim 3, wherein, relative to the compound of formula [2], the catalytic amount of the nickel compound used in (b) is from 0.50 to 1.00 mol % and the catalytic amount of the optically active compound of formula [3] used in (b) is from 0.60 to 1.20 mol %.

13. The process according to claim 1, wherein the reaction temperature is from −78° C. to the boiling point of a reaction solvent in (b).

14. The process according to claim 1, wherein the reaction temperature is from −20 to 25° C. in (b).

15. The process according to claim 2, wherein the reaction temperature is from 0 to 25° C. in (b).

16. The process according to claim 4, wherein the reaction temperature is from 0 to 25° C. in (b).

17. The process according to claim 1, wherein the reaction temperature is from −20 to 0° C. in (b).

18. The process according to claim 3, wherein the reaction temperature is from −20 to 0° C. in (b).

19. The process according to claim 3, wherein converting the compound of formula [4] to the compound of formula [5] in (c) comprises conversion under acidic conditions.

20. The process according to claim 4, wherein converting the compound of formula [4] to the compound of formula [5] in (c) comprises conversion under acidic conditions.

* * * * *

UNITED STATES PATENT AND TRADEMARK OFFICE
CERTIFICATE OF CORRECTION

PATENT NO. : 10,207,976 B2
APPLICATION NO. : 15/764598
DATED : February 19, 2019
INVENTOR(S) : Norikazu Otake et al.

It is certified that error appears in the above-identified patent and that said Letters Patent is hereby corrected as shown below:

In the Specification

In Column 12, Lines 45-50, and in Column 18, Lines 57-63,

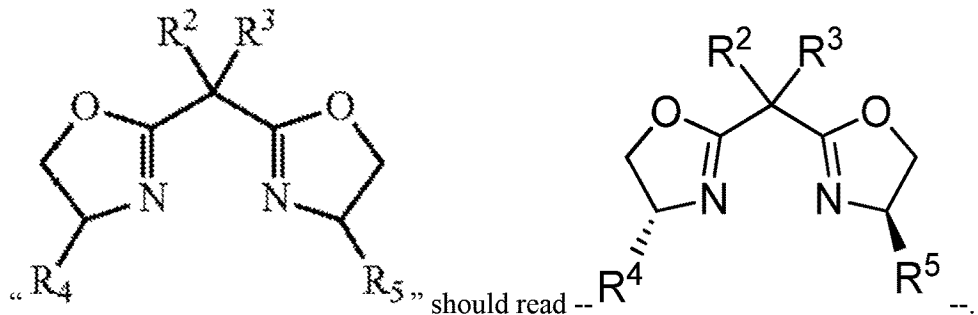

In the Claims

In Claim 1, Column 43, Lines 1-10, On the Title Page, in the Abstract (item (57)), In the Specification, in Column 4, Lines 27-33, in Column 6, Lines 48-55, and in Column 10, Lines 37-43,

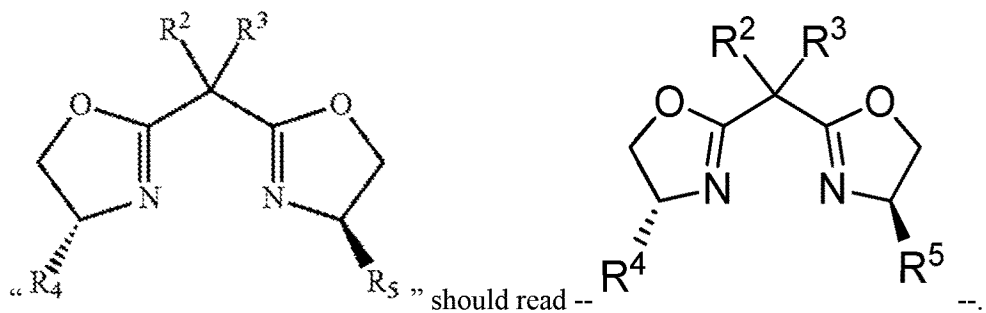

In Claim 1, Column 43, Line 30, "halo-$C_{3-6}$ alkyl" should read -- halo-$C_{1-6}$ alkyl --.

Signed and Sealed this
Thirtieth Day of April, 2019

Andrei Iancu
*Director of the United States Patent and Trademark Office*